United States Patent [19]

Hennart

[11] 3,976,769

[45] Aug. 24, 1976

[54] PESTICIDAL COMPOSITIONS CONTAINING PHOSPHORIC ESTERS AND DIVALENT SULPHUR COMPOUNDS

[75] Inventor: Claude Hennart, Aubervilliers, France

[73] Assignee: Airwick Industries, Inc., Carlstadt, N.J.

[22] Filed: Mar. 14, 1974

[21] Appl. No.: 451,381

Related U.S. Application Data

[62] Division of Ser. No. 180,137, Sept. 13, 1971, Pat. No. 3,836,643.

[30] Foreign Application Priority Data

Sept. 11, 1970 France .............................. 70.33014

[52] U.S. Cl. .................................. 424/175; 424/19; 424/32; 424/219
[51] Int. Cl.$^2$ ........................................... A01N 9/36
[58] Field of Search ................ 424/19, 27, 219, 175

[56] References Cited

UNITED STATES PATENTS

| | | | |
|---|---|---|---|
| 3,093,536 | 6/1963 | Loeffler ............................. | 424/219 |
| 3,097,128 | 7/1963 | Sprinkle et al. ...................... | 424/219 |
| 3,116,201 | 12/1963 | Whetstone .......................... | 424/219 |

FOREIGN PATENTS OR APPLICATIONS

261,923  5/1974  United Kingdom

OTHER PUBLICATIONS

Chemical Abstracts, vol. 56, (1962), p. 10635(b).
Chemical Abstracts, vol. 53, (1959), p. 11743c.

*Primary Examiner*—V. D. Turner
*Attorney, Agent, or Firm*—Wenderoth, Lind & Ponack

[57] ABSTRACT

Pesticidal composition comprising: a pesticidal, phosphoric ester the molecule of which has at least one alkyl group of 1 to 3 carbon atoms, 0.05 to 10% of an agent stabilizing the said ester against decomposition by protonisation, together with adjuvants characterized in that the stabilizing agent comprises at least one sulphur compound containing per molecule at least one divalent sulphur atom of which one valence is bonded to an atom chosen from sulphur, carbon, nitrogen, hydrogen, and metals capable of giving a salt, the other valence being bonded to an atom chosen from hydrogen, the carbon atom already noted, a second carbon atom, the nitrogen atom already noted, a second nitrogen atom, the metal atom already noted in the case of a metal of valence greater than one, a second atom of metal and oxygen when the first valence is not attached to an atom of hydrogen, the proportion of sulphur calculated with reference to the weight of the sulphur compound being between 5 and 99%. Process for stabilizing a phosphoric ester of which the molecule possesses at least one alkyl group containing 1 to 3 carbon atoms characterized in that there is added to the phosphoric ester or to a mixture which contains it, 0.05 to 10% calculated on the weight of the phosphoric acid ester of an agent capable of stabilizing the said phosphoric ester against protonisation and comprising at least one sulphur compound such as that defined thereupon.

7 Claims, No Drawings

PESTICIDAL COMPOSITIONS CONTAINING PHOSPHORIC ESTERS AND DIVALENT SULPHUR COMPOUNDS

This is a division of application Ser. No. 180,137, filed Sept. 13, 1971, now U.S. Pat. No. 3,836,643.

This invention concerns a process for stabilising pesticidal phosphoric esters, and compositions based on phosphoric esters so stabilised.

Phosphoric esters are nowadays very widespread for pesticidal use, particularly for insecticides. Their value is due principally to speed of action and the absence of accumulation of these compounds in living tissue as a result of their rapid hydrolysis in situ.

This latter characteristic which gives them a net advantage over the so called chlorinated pesticides, presents however a very grave inconvenience; the sensitivity of certain phosphoric esters to humidity, even simply that of the atmosphere, is such that their decomposition takes place without their being able to act on the pest organisms: the phosphoric esters which are sensitive are more particularly those which contain one or more low alkyl groups, such as methyl, ethyl, propyl or isopropyl groups attached to the phosphoric anion; this produces, on contact with molecules of water, an at least partial decomposition of these esters by protonisation, i.e. by displacement of one low alkyl group in favour of a hydrogen atom.

Among the sensitive phosphoric esters special mention should be made of O-2,2-dichlorovinyl- O,O-dimethylphosphate, better known under the common name DICHLORVOS and the abbreviation DDVP, the use of which in permanent insecticidal devices knon as evaporators has undergone a tremendous increase in recent years.

Various means of stabilisation have already been suggested for limiting the decomposition of these phosphoric esters but they are generally toxic, for example phenols, amines and low nitrogen heterocycles; another useful class of stabiliser comprises azoic and hydrozonic compounds but these have a strong colouration power so that they cannot always be used. The use of anhydrides or epoxides has also been used but it is known that these compounds act by fixation, either of a molecule of water or a molecule of free acid; it can be seen that this process is limited stoichiometrically and that the stabilisation ceases when all the stabiliser has entered into reaction; this leads to the necessity of using substantial proportions of these stabilisers which is not economic.

The present invention has as its object the stabilisation of pesticidal phosphoric esters by using substances more efficacious than those noted above and which do not possess the inconveniences: these substances are sulphur compounds; they are suitable in particular at relatively low concentrations for preserving phosphoric esters against protonisation. Thus the invention comprises pesticidal compositions comprising:

A. 5 to 99.95%, calculated on the weight of the composition, of a pesticidal, phosphoric ester the molecule of which has at least one alkyl group of 1–3 carbon atoms,
B. 0.05 to 10%, calculated on the weight of the phosphoric ester, of an agent stabilising said ester against decomposition by protonisation,
C. 0 to 90%, calculated on the weight of the composition, one of more solvents for the phosphoric ester, liquid or solid under pressure or otherwise, and
D. 0 to 50%, calculated on the weight of the composition of one or more inert adjuvants chosen from mineral adjuvants and organic adjuvants compatible with the phosphoric ester, said composition being characterised in that the stabilising agent comprises at least one sulphur compound containing per molecule at least one divalant sulphur atom of which one valence is bonded to an atom chosen from sulphur, carbon, nitrogen, hydrogen, and a metal capable of giving a salt, the other valence being bonded to an atom chosen from hydrogen, the carbon atom already noted, a second carbon atom, the nitrogen atom already noted, a second nitrogen atom, the metal atom already noted in the case of a metal of valence greater than one, a second atom of metal and oxygen when the first valence is not attached to an atom of hydrogen, the proportion of sulphur of sulphur calculated with reference to the weight of the sulphur compound being between 5 and 99%.

The present invention also includes a process for stabilising a phosphoric ester of which the molecule possesses at least one alkyl group containing 1–3 carbon atoms in admixture with 0.05 to 10% calculated on the weight of the phosphoric ester, of an agent stabilising the said ester against decomposition by protonisation, 0 to 90%, calculated on the weight of the composition, of one or more solvents for the phosphoric ester which are solid or liquid under pressure or otherwise and 0 to 50%, calculated on the weight of the composition, of one or more inert adjuvants selected from mineral adjuvants and organic adjuvants compatible with the phosphoric ester, the said process being characterised in that there is added to the phosphoric ester or to a mixture which contains it, 0.05 to 10% calculated on the weight of the phosphoric acid ester of an agent capable of stabilising said phosphoric ester against protonisation and comprising at least one sulphur compound such as that defined above.

The quantities of stabilising agent used according to the present invention are preferably between 0.05 and 4% based on the weight of the phosphoric ester.

In the sulphur compounds such as those defined according to the invention the valences of the atom of sulphur which are bonded to another atom or to other atoms in a molecule of the sulphur compound according to the invention can be constituted by a homopolar bond resulting from the displacement from a $\tau$ electron doublet, by one or two heteropolar bonds resulting from an exchange of electrons between the sulphur and the atom to which it is bonded or by one or two electrovalences resulting from electrostatic attraction between two ions of apposite polarity.

The sulphur compounds preferred for use in the present invention are as follows:

1. Sulfanes defined by formula I

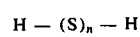  (I)

in which $n$ is a whole number between 1 and 6; such compounds are for example:
hydrogen monosulfide
hydrogen bisulfide
hydrogen trisulfide
hydrogen tetrasulfide
hydrogen pentasulfide hydrogen hexasulfide (sulphur content 98.9% by weight)

2. Mercaptans defined by formula II

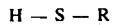 (II)

in which R is chosen from
i. a group Ra chosen from:
a. a phenyl group,
b. a benzyl group,
c. a phenyl group and a benzyl group bearing 1–3 substituents chosen from alkyl residues containing 1–6 atoms of carbon,
d. an alkyl group containing 1–18 carbon atoms,
e. a heterocyclic group chosen from monocyclic and bicyclic heterocyclic groups comprising 5 to 10 ring atoms in one or two fused rings, the first ring containing 1–3 ring members chosen from nitrogen, the group

and oxygen, the remaining ring members consisting of the groups

in whic R'' is a group chosen from hydrogen, phenyl, and an alkyl or cycloalkyl group containing 1–10 carbon atoms and R''' is hydrogen, phenyl, or an alkyl group containing 1–4 carbon atoms and the second ring being a benzene ring.
f. the groups (a) to (e) noted above carrying 1–3 substituents chosen from fluorine, chlorine and bromine and
g. the groups (a) to (e) noted above carrying a substituent chosen from carboxy, alkoxy carbonyl, mercaptoalkoxy carbonyl containing 2 to 6 atoms of carbon and an amino group

in which R' and R'' are the same or different and are chosen from hydrogen and alkyl residues containing 1–10 atoms of carbon and
ii. a group — A — S — H in which A is a group chosen from alkylene containing 2–13 carbon atoms, phenylene, toluylene and 1,2-bis(methylene carbonyloxy)ethylene.

Such compounds are for example the following:
Octadecanethiol
1,2-ethanedithiol
2-decyl-1,3-propanedithiol
butyl-2-mercapto acetate
pentyl-2-mercapto acetate
benzenethiol
4-bromo benzenethiol
4-fluoro benzenethiol
2,4,5-trichloro benzenethiol
2,4,6-tribromo benzenethiol
2-chloro propanethiol
bis-mercaptoacetate of ethane-1,2-diyl
methanethiol
butanethiol
dodecanethiol
1,10-decanedithiol
1,12-dodecanedithiol
benzylmercaptan
1,2-butanedithiol
1,4-butanedithiol
4-tertiobutyl benzenethiol
1,3-benzenedithiol
4-chloro benzenethiol
3,4-toluenedithiol
4,5-diphenyl-2-imidazolethiol
ethyl-2-mercapto acetate
methyl-3-mercapto propionate
2-mercapto benzoic acid
3-amino-5-mercapto-1,2,4-triazole
2-amino benzenethiol
2-N-decylamino ethanethiol
2-quinoleinethiol
2-mercapto benzoxazole
2-mercapto benzimidazole
2-mercapto pyridine
3-mercapto-1,2,4-triazole
2-N,N-diethylamino ethanethiol
5-chloro-2-mercapto benzimidazole
5,6-dichloro-2-mercapto benzimidazole
2-mercapto-1-methyl benzimidazole
1-butyl-2-mercapto benzimidazole
2-mercapto-2-phenyl benzimidazole
2-mercapto ethyl-2-mercaptoacetate
2-mercaptopentyl-3-mercapto propionate
2-mercapto-1-methyl imidazole 3. Sulfides defined by formula III:

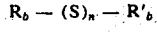 (III)

in which $R_b$ and $R'_b$ are independently chosen from:
a. an alkyl of 1 to 18 carbon atoms,
b. phenyl
c. benzyl
d. morpholinyl
e. piperidyl
f. pyridyl
g. benzothiazolyl
h. benzimidazolyl
i. benzoxazolyl
j. the groups (a) to (c) just mentioned carrying 1–3 substituents chosen from fluorine, chlorine, bromine, hyroxy, mercapto, nitro, cyano, carboxy, alkoxy carbonyl of 1–5 carbon atoms, and amino

as defined in 2 above and an alkyl containing 1–4 carbon atoms
and n represents a whole number between 1 and 6.
Such compositions are, for example, the following:
2-thia hexane
5-thia nonane
4-methylthio phenol
4-methylthio-3-methylphenol
2-methylthio benzimidazole
2-methylthio benzoxazole
benzylthiobenzene
4(4-amino phenylthio) nitrobenzene
methyl-3-methylthio propionate
4-methylthio-2,6-dimethylphenol 1-chloro-2-thia propane
methyl-4-thia valerianate
2-thia propyl benzene
bis(4-decylamino phenyl) sulfide
bis(4-dimethylamino phenyl) sulfide
bis(4-amino phenyl) sulfide
bis(2,4-hydroxy phenyl) sulfide
bis(2-amine phenyl) sulfide
didecyl sulfide
dioctadecyl sulfide
didodecyl sulfide
di-4-piperidyl sulfide
di-4-morpholinyl sulfide
diphenyl sulfide
bis(5-chloro-2-hydroxy-3-methyl phenyl) sulfide
bis(4-nitro phenyl) sulfide
bis(5-chloro-2-hydroxy phenyl) sulfide
bis(4-amino-4'-nitro phenyl) sulfide
bis(3,5-dichloro-2-hydroxy phenyl) sulfide
dimethyl disulfide
dioctyl disulfide
dibutyl disulfide
bis(2-mercapto ethyl) sulfide
didodecyl disulfide
dioctadecyl disulfide
dibenzyl disulfide
bis(ethoxy carbonyl) disulfide
2,3-dithia heneicosane
trichloromethylbithiobenzene
trichloromethylbi-4-thiofluorobenzene
trichloromethylbi-4-thiobromobenzene
1,4,5-trichloro-2-trichloromethylbithiobenzene
(2,3-dithiabutyl) benzene
2-dichlorofluoromethylbithiabenzothiazole
bis(4-dimethylamino phenyl) disulfide
bis(4-decylamino phenyl) disulfide
bis(2-hydroxy phenyl) disulfide
bis(4-chloro-2-hydroxy phenyl) disulfide
1,4-bis(pentoxycarbonyl)-2,3-dithia butane
4(4-aminophenyldithio) nitrobenzene
bis(4-nitrophenyl) disulfide
diphenyldisulfide
bis(2-cyano phenyl)disulfide
bis (2-carboxyphenyl) disulfide
bis(4-amino phenyl) disulfide
bis(2-amino-4-chloro phenyl) disulfide
4-dimorpholinyl disulfide
4-dipiperidyl disulfide
2-dipyridyl disulfide
4-dipyridyl disulfide
2-dibenzothiazoly disulfide
1,6-dimercapto-3,4-dithia hexane
1,4-dicyano-2,3-dithiabutane
1,4-dicarboxy-2,3-dithiabutane
1,6-dicarboxy-3,4-dithiahexane
1,4-bis(methoxycarbonyl)-2,3-dithiabutane
diphenyl trisulfide
2-dibenzothiazolyl trisulfide
2-dipyridyl trisulfide
bis(4-chlorophenyl) trisulfide
bis(2,4,5-trichloro phenyl) trisulfide
dibutyl trisulfide
dimethyl trisulfide
dibenzyl trisulfide
didodecyl trisulfide
dioctadecyl trisulfide
diisopropyl trisulfide
2-dibenzothiazolyl trisulfide 2-dipyridyl tetrasulfide
dibutyl tetrasulfide
didodecyl tetrasulfide
dioctadecyl tetrasulfide
diphenyl tetrasulfide
2-dibenzothiazolyl tetrasulfide
ditertbutylpentasulfide
ditertdodecylpentasulfide
bis(4-chloro phenyl) pentasulfide
ditertdodecylhexasulfide
didecylhexasulfide
dipropylhexasulfide
dioctadecylhexasulfide
dibenzylhexasulfide
bis(4-dimethylamino phenyl) hexasulfide
bis(4-nitrophenyl) hexasulfide
2-piperidino thiobenzothiazole
2-mercapto benzothiazole
2-morpholinothio benzothiazole
3-thiaglutaric acid
butyl-3-thiaglutarate
methyl-5-thiapimelate
isopropyl-2,4-diethyl-3-thiaglutarate
3-thiaglutaronitrile 4a. Heterocyclic compounds which comprise 5 to 23 ring members forming 1 to 5 rings with at most 2 to 3 fused rings, which comprise 1–3 rings which each contain an —S— chain member and 2 other chains members chosen from the groups

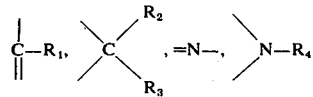

the remainder of the chain members being chosen from among the groupings

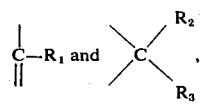

the heterocyclic compounds with fused rings being chosen from among those of which all the hetero chain members are contained in one and the same ring, this ring being the central ring in the case of 3 fused rings, all the ring members being chosen taking into account that all the valences of the heterocyclic compound should be saturated, $R_1$, $R_2$ and $R_3$ being independently chosen from hydrogen, chlorine, bromine, fluorine, alkyl of 1–5 carbon atoms, trifluoromethyl, nitro, and

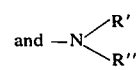

as defined under 2 above, the group

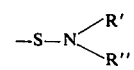

in which R' and R" are the same or different and are hydrogen, phenyl or alkyl of 1–18 carbon atoms, alkanoyl amino containing 1–4 carbon atoms, mercapto, alkyl thio containing 1–18 carbon atoms, the oxo oxygen, thioxo, phenylazo, phenylazo carrying 1–2 substituents chosen from methyl, chloro, nitro and methoxy, and R$_4$ being chosen from hydrogen and methyl.

These heterocyclic compounds can be chosen from amongst: the thiazoles, benzothiazoles, thiazolines, thiazolidines, thiadiazoles, thiadiazolines, thiadiazolidines, phenothiazines, and tetrahydrothiophenes. Such compounds are for example the following:

tetrahydrothiophene
2-amino thiazoline
2-amino thiazole
2-acetamido thiazole
2-amino-4-methyl thiazole
2-acetamido-4-methyl thiazole
2-amino-4-phenyl thiazole
2-amino-5-nitro thiazole
2-amino-5-chloro thiazole
benzothiazole
2-methyl benzothiazole
2,5-dimethyl benzothiazole
2-amino benzothiazole
2-amino-4-chloro benzothiazole
2-amino-6-chloro benzothiazole
2-methylthio benzothiazole
2-methylthio benzimidazole
2,5-bis(4-pyridyl)-1,3,4-thiadiazole
phenothiazine
2-chloro phenothiazine
2-trifluoromethyl phenothiazine
2-methoxy phenothiazine
3-methyl-2-oxo benzothiazolidine
2-mercapto benzothiazole
5-chloro-2-mercapto benzothiazole
2-mercapto thiazole
2-mercapto-1,3,4-thiadiazole
2,5-dimercapto thiadiazole
2-mercapto-4-phenyl-1,3,4-thiadiazole
2-mercapto-4-methyl-1,3,4-thiadiazole
5-amino-2-mercapto-1,3,4-thiadiazole
N-methyl benzothiazolethione-2
N-methyl thiazolethione-2-
N-methyl thiazolidinethione-2
4-butyl N-methyl thiazolinethione-2
4-oxo-2-thioxo thiazolidine
3-ethyl-4-oxo-2-thioxo-thiazolidine
3-methyl-4-oxo-5-phenylazo-2-thioxo thiazolidine
3-methyl-5(4-nitro phenylazo)-4-oxo-2-thioxo thiazolidine
5(4-methoxy phenylazo)-4-oxo-2-thioxo thiazolidine
5-(2-methyl phenylazo)-4-oxo-2-thioxo thiazolidine
5-(2-chloro phenylazo)-4-oxo-2-thioxo thiazolidine
5-(2,4-dichloro phenylazo)-4-oxo-2-thioxo thiazolidine
5-(2-chloro-4-nitro phenylazo)-4-oxo-2-thioxo thiazolidine
5-mercapto-3-phenyl-2-thioxo-1,3,4-thiadiazolidine
2-methylaminothio benzothiazole
2-dimethylaminothio benzothiazole
2-butylaminothio benzothiazole
2-cyclohexylaminothio benzothiazole
2-decylaminothio pyridine
2-octadecylaminothio-4-phenyl-1,3,4-thiadiazole
2-(4-thiazolyl) benzimidazole
2-(2-methyl-4-thiazolyl) benzimidazole
2-(2-thiazolyl) benzimidazole
2-(2-thiazolinyl) benzimidazole
2-[(4-thiazolyl) methyl]benzimidazole
2-(2-thiadiazol-1,3,4-yl) benzimidazole
3-phenyl-1,3,4-thiadiazolidine-2,5-dithione
3-ethyl-1,3,4-thiadiazolidine-2,5-dithione 4b. Monocyclic heterocyclic compounds chosen from saturated heterocyclic compounds with 6 ring members which 1–3 ring members which are not contiguous are constituted by sulphur, one other ring member being chosen from the groups

and

and the remainder of the ring members being chosen from the groups

in which R$_2$, R$_3$ and R$_4$ have the definition given in (4a) above. These heterocyclic compounds can be chosen from amongst dithianes, trithianes and thiomorpholines.

Such compounds are for example the following:
1,4-dithiane
1,3,5-trithiane
2,4,6-trimethyl-1,3,5-trithiane
thiomorpholine
3-oxo thiomorpholine
3-thioxo thiomorpholine
3-mercapto thiomorpholine
3-bromo-N-methyl thiomorpholine
2,4,6-trinitro-1,3,5-trithiane
3-amino thiomorpholine
3-decylaminothio thiomorpholine
2-acetamido-1,3,4-trithiane
2-octadecylaminothio-1,3,4-trithiane
3-(4-methoxy phenylazo) thiomorpholine
3-(2,4-dichloro phenylazo) thiomorpholine
3-(2-methyl phenylazo) thiomorpholine 5. Thioic compounds defined by formula IV:

in which R$_c$, Y, X and Q are chosen from those defined under (a), (b) and (c):

a. the compounds in which R$_c$ and Q form two distinct groups and in which R$_c$ is a group chosen from hydrogen, alkyl or 1–6 carbon atoms and an alkyl residue as just mentioned bearing a substituent chosen from carboxy, alkoxy carbonyl having 2 to 5 carbon atoms, cyclo alkyl or alkyl cyclo alkyl containing 6 to 10 carbon atoms, phenyl, benzyl, or alkenyl containing 2 to 5 carbon atoms and X and Y represent an atom chosen from oxygen and sulphur, at least one of them per molecule being a sulphur atom; Q is chosen from among α - a group R$_c$' selected from an alkyl containing 1 to 6 carbon atoms an alkyl carrying a group cyano, cycloalkyl containing 6 to 10 carbon atoms, alkyl cycloalkyl containing 6 to 10 carbon atoms, pyridyl, phenyl, and phenyl bearing one to three substituents chosen from fluorine, bromine, alkyl of 1 to 4 carbon atoms, nitro, and hydroxy β - a group

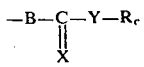

in which X, Y and $R_c$ have the definition given above and in which B is chosen from sulphur, a disulphid group and a hydrocarbon divalent group chosen from alkylenes containing 1 to 8 carbon atoms and 1,2-, 1,3- and 1,4-phenylenes. γ - a group $— Z — R_c''$ chosen among groups in which Z is oxygen or sulphur and $R_c''$ is a group chosen from those defined for $R_c$;

b. the compounds in which $R_c$ and Q form together an alkylene group containing 3 to 10 carbon atoms in branched or straight chains c. and compounds in which Q represents the group $— Z — R_c''$ and in which $R_c$ and $R_c''$ together form a divalent group chosen from aliphatic hydrocarbon chains containing 2 to 6 carbon atoms, 1,2, 1,3,- and 1,4-phenylenes, cyclic systems containing 5 to 10 ring members and one or two rings, under which one of the two ring members are chosen from the group hydrocarbons, the group = N — and the group

Such compounds are for example the following:
thioacetic acid
thiopropionic acid
thiobutyric acid
dithiobutyric acid
dithioacetic acid
hexanethioic acid
hexanedithioic acid
hexane 1,6-bis thioic acid
cyclohexene carbodithioic acid
thiobenzoic acid
dithiosalicylic acid
2,6-dichloro thiobenzoic acid
2-chlor-6-methyl thiobenzoic acid
2-chloro-6-nitro thiobenzoic acid
thionicotinic acid
dithioterephthalic acid
ethyl thioacetate
methylthiobenzoate
benzylthioacetate
diethyldithiolcarbonate
diphenyldithiocarbonate
ethanediyle-1,2-bis(dithiocarbonate)
dibenzyltrithiocarbonate
dimethyltrithiocarbonate
thiophenylacetic acid
dibutyltrithiocarbonate
1,2-ethylene trithiocarbonate
bis(carboxymethyl) trithiocarbonate
bis(3-carboxypropyl) trithiocarbonate
bis(methoxycarbonylmethyl) trithiocarbonate
bis(butoxycarbonylmethyl) trithiocarbonate
dihexyltrithiocarbonate
dioctyltrithiocarbonate
acetonitrile-0-isopropylthiocarbonate
1,2-phenylene trithiocarbonate
2,3-quinoxalinediyletrithiocarbonate
butyl ethyl xanthate
methyl ethyl xanthate
phenyl ethyl xanthate
cyclohexylethyl xanthate
menthylethylxanthate
benzylethylxanthate
allylethylxanthate
methylbutylxanthate
methylcyclohexyl xanthate
ethylbenzylxanthate
butylallylxanthate
methylphenylxanthate
phenylphenylxanthate
ethoxythiocarbonyl sulfide
methoxythiocarbonyl disulfide
ethoxythiocarbonyl disulfide
gamma thiobutyrolactone
gamma thioundecalactone
1,3-phenylene trithiocarbonate
isopropyl thiocarbonyl disulfide
methyl(4-butylcyclohexyl) xanthate
dicyclohexyltrithio carbonate
divinyltrithio carbonate 6. Thiamides defined by formula V:

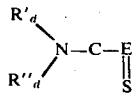

in which $R'_d$, $R''_d$ and E are chosen as defined under (a) and (b):

a. $R'_d$ and $R''_d$ are each separately chosen from hydrogen, alkyl of 1 to 4 carbon atoms, phenyl and taken together from an alkylene, straight or branched chain group containing 4 to 10 carbon atoms, E represents a group chosen from a group $R_d$ as defined under $R'_c$ in 5) a group

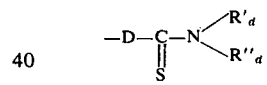

in which D represents a symbol chosen from a direct bond or a divalent hydrocarbon group chosen from alkylenes containing 1 to 8 carbon atoms and phenylenes and in which $R'_d$ and $R''_d$ have the same meaning as above b. $R_d'$ and E represent together a group such as defined under (b) in 5.

Such compositions are, for example, the following:
thioacetamide
N,N-dimethyl thioacetamide
N,N-dibutyl thioacetamide
thiobenzamide
2,6-dichloro thiobenzamide
2,6-dihydroxy-N-ethylthiobenzamide
2,6-dichloro-N-ethyl thiobenzamide
2-chloro-6-methyl thiobenzamide
2,3,6-trichloro thiobenzamide
2-chloro-6-nitro thiobenzamide
2-chloro-4-terbutyl thiobenzamide
2-chloro-6-fluoro thiobenzamide
2-chloro-6-bromo thiobenzamide
thioformamide
thionicotinamide
thioisonicotinamide
N-thioacetylpiperidine
thioheptanoylamide N-thioacetylpyrrolidine
dithio malonamide
4-N-thioacetylpipecoline
N,N-dimethylthiohexanoylamide
dithioxamide
dithiosuccinamide
dithioadipamide
dithiosebacamide
N,N,N',N'-tetramethyl dithioadipamide
N,N'-diethyl dithioadipamide
N-phenyl thioacetamide
N-methyl N-phenyl thioacetamide
dithiosuccinoyl bis-1,1' (piperidine)
gamma, thiobutyrolactam
epsilon thiocaprolactam
gamma thioundecalactam 7. Dithiocarbamic esters defined by formula VI:

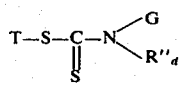 (VI)

in which R''$_d$ is chosen from hydrogen, alkyl of 1 to 4 carbon atoms and phenyl and in which T represents a group chosen from a. a group R$_d$ chosen from an alkyl containing 1 to 12 carbon atoms, alkenyl containing 2 to 12 carbon atoms, benzyl, cycloalkyl or cycloalkenyl containing 5 to 6 carbon atoms, cycloalkyl and cycloalkenyl such as defined above bearing 1 to 3 alkyl substituents each containing 1 to 4 carbon atoms, phenyl and a phenyl group carrying 1 to 3 substituents chosen from alkyl and alkenyl groups containing 1 to 5 carbon atoms, chlorine and nitro;

a group 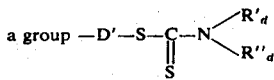 b)

in which D' is alkylene straight or branched chain containing 2 to 6 carbon atoms and R'$_d$ and R''$_d$ are chosen such as defined in 6, and in which G is chosen from a group R'$_d$ which has one of the meanings given for R''$_d$ defined above and a group

in which D', R$_d$ and R''$_d$ have the definition given above.

Such compounds are, for example, the following:
ethyl-N-methyl dithiocarbamate
ethyl-N,N-dimethyl dithiocarbamate
methyl-N,N-dibutyl dithiocarbamate
methyl-N,N-diethyl dithiocarbamate
ethyl N-methyl N-phenyl dithiocarbamate
methyl N-ethyl N-phenyl dithiocarbamate
methyl N,N-pentamethylene dithiocarbamate
ethyl N,N-tetramethylene dithiocarbamate
allyl N,N-dimethyl dithiocarbamate
dodecyl N,N-dimethyl dithiocarbamate
cyclohexyl N,N-dimethyl dithiocarbamate
cyclopenten-2-yl-N-methyl dithiocarbamate
menthyl N,N-dimethyl dithiocarbamate
phenyl N,N-dimethyl dithiocarbamate
2,4-dinitrophenyl N,N-dipropyl dithiocarbamate
2,4-dinitrophenyl N-ethyl N-methyl dithiocarbamate
benzyl N,N-dimethyl dithiocarbamate
4-chlorophenyl, N,N-dimethyl dithiocarbamate
4-tertbutylphenyl N,N-dimethyl dithiocarbamate
4-pentyl phenyl N,N-dimethyl dithiocarbamate
4(penten-2-yl)phenyl N,N-dimethyl dithiocarbamate
N,N'-ethylene bis (methyl dithiocarbamate)
N,N'-ethylene bis (butyl dithiocarbamate)
N,N'-ethylene bis (2,4-dinitro phenyl dithiocarbamate)
N,N'-(2,3-butanediyl) bis (ethyl dithiocarbamate)
N,N'-(3,4-hexanediyl) bis (ethyl dithiocarbamate)
N,N'-ethylene bis (dodecyl dithiocarbamate)
1,2-ethane diyl bis(N,N-dimethyl dithiocarbamate)
1,2-butane diyl bis(N,N-dimethyl dithiocarbamate)
1,4-butane diyl bis(N,N-diethyl dithiocarbamate)

8. Thiocarbamic esters defined by formula VII:

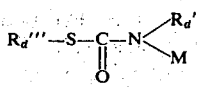 (VII)

in which R$_d$''' is chosen from alkyl of 1 to 18 carbon atoms cyclo alkyl or alkyl cycloalkyl of 6 to 10 carbon atoms, phenyl and phenyl carrying 1 to 3 substituents chosen from chlorine, nitro, and alkyl containing 1 to 4 carbon atoms, 2-benzimidazolyl, 2-benzoxazolyl and 2-benzothiazolyl and R$_d$' and M are chosen as defined under (a) and (b):

a. R$_d$' is chosen from groups defined for R$_d$'' in 7 and M is a group chosen from the group R$_d$' defined above, the group

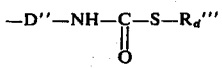

in which D'' is chosen from a 1,2-, 1,3-, or 1,4-phenylene group and a 1,2-, 1,3- and 1,4-phenylene group substituted by methyl and R$_d$''' has the signification given above.

b. R$_d$' and M represent together an alkylene group containing 6 to 9 carbon atoms.

Such compositions are for example the following:
N-methylcarbamoylthiomethane
N,N-dimethylcarbamoylthiobutane
N-butylcarbamoylthiododecane
N-phenylcarbamoylthiooctadecane
1-N,N-diethylcarbamoylthio 2,5-dimethyl cyclohexane
1-N,N-diethylcarbamoylthio 2,5-diethyl cyclohexane
N-ethylcarbamoylthiobenzene
1-N-propylcarbamoylthio-4 nitro benzene
1-piperidinocarbamoylthio 2,4,5-trichloro benzene
1-(1-perhydroazecinyl) carbonylthio 2,5-dimethyl benzene
1-(1-perhydroazepinyl) carbonylthio 4-tertiobutyl benzene
2-N-phenylcarbamoylthio benzimidazole
2-N-butylcarbamoylthio benzoxazole
2-N-propylcarbamoylthio benzothiazole
1,2-bis(methylthiocarboxamido) benzene
1,4-bis(phenylthiocarboxamide) benzene
1,4-bis(benzothiazolyl-2 thiocarboxamido) benzene
2,4-bis(butylthiocarboxamido) toluene
2,4-bis(cyclohexylthio carboxamide) toluene 2-N-(3-chloro phenyl) carbamoylthio benzimidazole methyl N,N-dibenzyl thiocarbamate 9. Thiuram compounds defined by formula VIII:

$$\begin{matrix} R_d' \\ R_d'' \end{matrix} \!\! > \!\! N\!\!-\!\!\underset{\underset{S}{\|}}{C}\!\!-\!\!(S)_n\!\!-\!\!\underset{\underset{S}{\|}}{C}\!\!-\!\!N \!\! < \!\! \begin{matrix} R_d' \\ R_d'' \end{matrix} \qquad (VIII)$$

in which n is a whole number between 1 and 6, $R_d'$ and $R_d''$ are chosen as given under 6 or in such a fashion that both $R_d'$ on the one hand and and two $R_d$ on the other hand form together a phenylene group, an alkylene group containing 2 to 3 carbon atoms. Such compounds are for example as follows:

bis (thiocarbamoyl) disulphide
bis (N,N-dimethyl thiocarbamoyl) sulphide
bis (N,N-diethyl thiocarbamoyl) sulphide
bis(N,N-diethyl thiocarbamoyl) sulphide
bis(N-methyl thiocarbamoyl) disulphide
bis(N,N-dimethyl thiocarbamoyl) disulphide
bis(N-ethyl thiocarbamoyl) disulphide
bis(N,N-diethyl thiocarbamoyl) disulphide
bis(N-methyl N-phenyl thiocarbamoyl) disulphide
bis(N,N-diphenyl thiocarbamoyl) disulphide
bis(N,N-dibutyl thiocarbamoyl) disulphide
bis(N,N-pentamethylene thiocarbamoyl) sulphide
bis(N,N-tetramethylene thiocarbamoyl) disulphide
bis(N,N-pentamethylene thiocarbamoyl) disulphide
bis(N,N-tetramethylene thiocarbamoyl) disulphide
bis(N,N-dimethyl thiocarbamoyl) tetrasulphide
bis(N,N-pentamethylene thiocarbamoyl) tetrasulphide.
bis(N,N-dimethyl thiocarbamoyl) hexasulphide
1,3,6-perhydrothiadiazepine 2,7-dithione (a)
1,2,4,7-perhydrodithiadiaz.cine 3,8-dithione (a')
1,2,3,5,8-perhydrotrithiadiazonine 4,9-dithione (a'')
2,4,9-trithioxo 1,2,3,5,8-perhydrotrithia diazonine (b)
2,4,10-trithioxo 1,2,3,5,9-perhydro trithia diazecine (b')
6,9-ethano 2,4,11-trithioxo -perhydrotrithiadiazonine -trithia 5,10-diaza cycloundeca-6,8-diene (b'')
5-ethano-2,4,9-trithioxo 1,2,3,5,8-perhydrotrithiandiazonine (b''')
a. compound commonly called ethylenethiuram sulphide
a'. compound commonly called ethylene thiuram disulphide
a''. compound commonly called ethylene thiuram trisulphide
b. compound commonly called ethylene thiuram tetrasulphide
b'. compound commonly called propylene thiuram tetrasulphide
b''. compound commonly called paraphenylene thiuram tetra sulphide
b'''. compound commonly called piperazine thiuram tetrasulphide.

10. Isothiocyanic esters defined by the formula IX:
$$R_e - N = C = S$$

in which $R_3$ is chosen from alkyl of 1 to 8 carbon atoms, phenyl and phenyl carrying 1 to 3 substituents chosen from alkyl of 1 to 5 carbon atoms, fluorine, chlorine, bromine, alkoxy and alkyl thio groups containing 1-4 carbon atoms and nitro.

Such compositions are, for example, the following:
methyl isothiocyanate
ethyl isothiocyanate
isopropyl isothiocyanate
butyl isothiocyanate
octyl isothiocyanate
phenyl isothiocyanate
4-chlorophenyl isothiocyanate
2,4-dichlorophenyl isothiocyanate
2-fluorophenyl isothiocyanate
4-bromophenyl isothiocyanate
4-nitrophenyl isothiocyanate
3-cresyl isothiocyanate
4-tertbutylphenyl isothiocyanate
2-methyl-4-tertbutylphenyl isothiocyanate
anisyl isothiocyanate
4-methylthiophenyl isothiocyanate
4-isobutoxyphenyl isothiocyanate
4-pentylphenyl isothiocyanate 11. Thio ureas defined by the formula X:

$$\begin{matrix} R_f'' \\ R_f''' \end{matrix} \!\! > \!\! N\!\!-\!\!\underset{\underset{S}{\|}}{C}\!\!-\!\!N \!\! < \!\! \begin{matrix} R_f \\ W \end{matrix} \qquad (X)$$

in which $R_f'''$ is hydrogen, allyl, phenyl, or alkyl of 1–4 carbon atoms and W is chosen in one of the ways defined under (a) and (b).

a. W represents a group $R_f'$ chosen from hydrogen, alkyl of 1–4 carbon atoms and allyl, and $R_f$ and $R_f''$ taken separately represent groups $R_f'$ defined above and taken together represent ethylene group and b. W represents a group $$-D''-NH-\underset{\underset{S}{\|}}{C}-NH-R_f''''$$

in which D'' is as defined in 8, $R_f''''$ is selected from an alkoxy carbonyl residue containing 2 to 5 carbon atoms and $R_f$ and $R_f''$ represent hydrogen.

Such compounds are, for example, the following:
thiourea
N-methylthiourea
N,N-dimethylthiourea
N,N'-dimethylthiourea
N,N,N'-trimethylthiourea
tetramethylthiourea
N-ethylthiourea
N,N-diethylthiourea
N,N'-diethylthiourea
N-propylthiourea
N,N-dipropylthiourea
N-isopropylthiourea
N-butylthiourea
N-isobutylthiourea
N-secbutylthiourea
N-tertiobutylthiourea
N-allylthiourea
N,N'-diallylthiourea
N-phenylthiourea
1,2-bis(N'-ethoxycarbonyl thiourea) benzene
1,2-bis(N'-methoxycarbonyl thiourea) benzene
1,2-bis(N'-butoxycarbonylthiourea) benzene
1,2-bis(N'-ethoxycarbonylthiourea) benzene
1,2-bis(N'-propoxycarbonylthiourea) toluene
1,3-bis(N'-isopropoxycarbonylthiourea) benzene 2-thioxo imidazolidine (c)
c. product commonly called ethylene thiourea.
12. Thiiranes defined by formula XI:

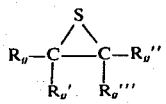

in which $R_a$, $R_a'$, $R_a''$ and $R_a'''$ are chosen from the groups selected under (a) and (b)

a. $R_a$ is hydrogen, alkyl of 1–6 carbon atoms, methyl bearing one chlorine atom, phenyl, phenyl bearing one chlorine atom, alkoxy of 1–4 carbon atoms, phenoxy, phenoxy carrying one or two substituents chosen from chlorine and methyl, $R_a'$, $R_a''$ and $R_a'''$ are the same or different and are hydrogen or methyl.

b. $R_a$ is chosen from 8-carboxyoctyl and 8-alkoxycarbonyloctyl in which the alkoxy group contains 1–8 carbon atoms, $R_a'$ and $R_a'''$ are each hydrogen and $R_a''$ is octyl or 2,3-epithiooctyl.

Such compounds are, for example, the following:
thiirane
2-methyl thiirane
2-ethyl thiirane
2,2-dimethyl thiirane
2,3-dimethyl thiirane
2,2,3-trimethyl thiirane
2-butyl thiirane
2-hexyl thiirane
2-methoxymethyl thiirane
2-ethoxymethyl thiirane
2-isopropoxymethyl thiirane
2-butoxymethyl thiirane
2-phenoxymethyl thiirane
2-phenyl thiirane
2-(4-chloro phenyl) thiirane
2-(4-chlorophenoxymethyl) thiirane
2-(2,4-dichlorophenoxymethyl) thiirane
2-(4-methylphenoxymethyl) thiirane
2-chloromethyl thiirane
9,10-epithio stearic acid
9,10,12,13-bis-epithio-stearic acid
methyl 9,10-epithio stearate
butyl 9,10-epithio stearate
octyl 9,10-epithio stearate
ethyl 9,10,12,13-bis-epithio stearate 13. Sulfenamides defined by formula XII:

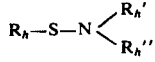

in which $R_h$ is chosen from methyl, methyl bearing 1–3 substituents selected from chlorine and fluorine, ethyl, and ethyl bearing 1–5 substituents chosen from chlorine and fluorine.

$R_h'$ and $R_h''$ are chosen in one of the ways defined under (A), (B) and (C):

A. $R_h'$ and $R_h''$ are hydrogen, alkyl of 1–4 carbon atoms, phenyl or cyclohexyl.

B. $R_h'$ and $R_h''$ are chosen from the groups (A) and (B) as defined, the group chosen in the group (B) being chosen from methylsulfonyl, ethylsulfonyl, phenylsulfonyl, chlorophenyl, and $-SO_2-NX'X''$, in which $X'$ and $X''$ are selected from methyl ethyl and phenyl.

C. $R_h'$ and $R_h''$ form together a cyclic system selected from (a) a cyclic system comprising 1–10 ring members and 1 or 2 rings in which the nitrogen atom is one of the ring members, a second ring member being chosen from a hydrocarbon member, sulphur, oxygen and nitrogen and the other ring members being hydrocarbon ring members. (b) a cyclic system as defined under (a) and carrying one or two carbonyl oxygen atoms.

Such compounds are, for example, the following:
N-(ethylthio) butylamine
N-(methylthio) butylamine
N-(trichloromethylthio) dibutylamine
N-(trichloromethylthio) dicyclohexylamine
N-(trichloromethylthio) succinimide
N-(trichloromethylthio) phthalimide
N-(trichloromethylthio) benzoxazolone
N-(trichloromethylthio)benzothiazolone   N-(trichloromethylthio) benzothiazoline
N-(trichloromethylthio) benzimidazolone
N-(dichlorofluoromethylthio) tetrahydrophthalimide
N-(dichlorofluoromethylthio) phthalimide
N-(1,1,2,2-tetrachloroethylthio) tetrahydrophthalimide
N-(trichloromethylthio)N-(methylsulfonyl)4-chloroaniline
N-(trichloromethylthio) N-(ethylsulfonyl) aniline
N-(trichloromethylthio) N-(phenylsulfonyl) aniline
N-(trichloromethylthio) N-(diethylsulfamoyl) propylamine
N-(dichlorofluoromethylthio) N-(dimethylsulfamoyl) aniline
N-(trichloromethylthio) N-methylphenyl sulfamoyl) methylamine
N-(methylthio) aniline
N-(chloromethylthio) dipropylamine
N-(trifluoromethylthio) cyclohexylamine
N-(2-chloro-1,1,2,2-tetrafluoroethylthio) phthalimide
N-trichloromethylthiotetrahydrophthalimide
N-(ethylthio) diphenylamine
N-(trichloromethylthio) dimethylamine 14. Sulfenic esters defined by formula XIII:
$$R_h - S - O - R_h''' \qquad (XIII)$$
in which $R_h$ is as defined in 13 and $R_h'''$ is selected from phenyl, phenyl carrying 1–3 substituents chosen from chlorine, nitro, and alkyl and alkoxy containing 1–4 carbon atoms, naphthyl and quinolyl.

Such compounds are, for exmaple, the following:
phenylethane sulfenate
phenyltrichloromethane sulfenate
2,4,5-trichlorophenyl trichloromethane sulfenate
3,5-dimethoxyphenyl trichloromethane sulfenate
4-nitrophenyl trichloromethane sulfenate
4-methoxy-3-tertbutylphenyl trichloromethane sulfenate
3,5-dimethylphenyl trichloromethane sulfenate
4-butoxyphenyl trichloromethane sulfenate
2-naphthyl trichloromethane sulfenate
1-naphthyl dichlorofluoromethane sulfenate
3,5-dimethoxyphenyl dichlorofluoromethane sulfenate
4-methoxyphenyl 1,1,2,2-tetrachloroethane sulfenate
4-quinolyl 1,1,2,2-tetrachloroethane sulfenate
8-quinolyl trichloromethane sulfenate
8-quinolyl ethane sulfenate
2-naphthyl methane sulfenate 2,4-dichlorophenyl chloromethane sulfenate
4-chloro-2-methylphenyl trifluoromethane sulfenate
phenyl 2-chloro-2,2-difluoroethane sulfenate
8-quinolyl-2-chloro-1,1,2,2-tetrafluoroethane sulfenate 15. Thio ketones defined by formula XIV:

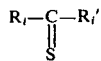 (XIV)

in which $R_i$ and $R_i'$ are chosen from alkyl of 1–4 carbon atoms, alkyl of 1–4 carbon atoms carrying 1–9 fluorine atoms, cyclohexyl, phenyl, and phenyl carrying 1 or 2 substituents selected from alkyl and alkoxy groups containing 1–4 carbon atoms.

Such compounds are, for example, the following:
thioacetone
2-thioxobutane
3-thioxopentane
4-thioxoheptane
2,6-dimethyl-4-thioxoheptane
thioacetylcyclohexane
dicyclohexylthioketone
1,3-difluorothioacetone
perfluorothioacetone
4-perfluoroheptanethione
2-perfluorohexanethione
1,1,1,3,3,4,4-heptafluorobutane-2-thione
thioacetophenone
thiobutyrophenone
cyclohexylcarbothioylbenzene
2,4-dimethylthioacetophenone
o.methoxy thiopropiophenone
4-methoxy-2-methyl thioacetophenone
4,4'-dimethoxy thiobenzophenone
2,2',4,4'-tetramethoxy thiobenzophenone
2,2'-dimethyl thiobenzophenone
2,2',4,4'-tetramethyl thiobenzopheneon
p.butoxyacetophenone
2,4-dibutyl thioacetophenone 16. Derived salts
of mercaptans defined in 2 and 4,
of thioic acids defined in 5,
of sulphanes defined in 1
of acids corresponding to the thio carbamic esters defined in 7 and 8
in which the cationic portion is selected from metals such as sodium, potassium, calcium, zinc, cadmium, copper, nickel, cobalt, iron, manganese, silver, lead, barium, strontium and aluminum and an ammonium ion chosen from ions derived from ammonia and ions derived from amines containing 1–3 groups chosen from alkyl groups of 1–4 carbon atoms and phenyl groups such as, for example, methylamine, dimethylamine, trimethylamine, diethylamine, triethylamine, butylamine, dibutylamine, tributylamine, methylaniline and dimethylaniline and ions derived from a nitrogen heterocycle such as pyridine, morpholine, N-methylmorpholine, piperidine and pipecolines.

The use of these salts is particularly valuable when the phosphoric ester used has already undergone protonisation, the salt introduced as stabiliser then acting in a first stage to neutralize the acid phosphoric ester by exchanging its cation therewith against a proton; this neutralization is favourable to the stabilisation since it has been noted by the applicants that the conservation of phosphoric esters is better when they do not contan any acid by-products; the sulphur compound now having lost its cation preserves its stabilising properties and then acts for a second time.

The solvents for the phosphoric ester can advantageously be hydrocarbons of the aliphatic, alicyclic or aromatic series which are solid or liquid at ambient temperature under pressure or otherwise. Such solvents may be used separately or in admixture. Their solvent power for the phosphoric ester and/or the stabiliser may be optionally reinforced by the addition of co-solvents which may be chosen from the groups of aliphatic ketones, hydroxylated compounds, ethers, esters, amides, nitriles and halogenated hydrocarbons.

Other solvents usable in compositions according to the present invention are halogenated hydrocarbons, ethers and esters formed by aliphatic, cyclo aliphatic or aralcoylic alcohols or phenols and aliphatic acids or di acids such as phthalic acid, sebacic acid and adipic acid, or again phosphoric esters which are not pesticides such as the phosphoric triesters of methyl, ethyl, butyl, octyl, decyl, dodecyl, phenyl, cresyl, diphenyl, tert.butylphenyl. The solvents usable in the compositions according to the present invention can also be solid compounds such as, for example, organic synthetic resins, such as homopolymers and copolymers formed starting from vinyl derivatives (acetate, propionate, butyrate, oxides, formal, acetal, butyral, chloride, etc.) and/or vinylidene derivatives and/or alkenes (ethylene, propylene, butylene) and/or styrene and/or vinyl pyrolidones, and/or cellulose derivatives (methyloxide, ethyloxide, benzyloxide, acetate, propionate, butyrate, phthalate, nitrate) and/or isoprene, and/or butadiene and/or acrylic or methacrylic esters and/or allyl esters (phthalate, isophthalate, maleate, cyanurate), such organic resins can also be obtained by interaction of compounds with reactive groupings, as for the so-called "epoxy" resins resulting from the condensation of an epoxide on a polyphenol, polyester resins resulting from the action of a poly acid on a polyol, and polyurethanes resulting from the condensation of a polyisocyanate with a polyol of coumarone indene resins.

Solid compounds able to serve as solvents can also be natural resins, such as colophane, shellac, tallol or a waxy resin.

Among inert mineral adjuvants which may be used in compositions according to the present invention the following should be noted: brick, pumice, vermiculite, dried clay, calcium carbonate, pyrophylite, dolomite, glass fibre, plaster, talc, natural silica, fossil or otherwise, artificial silica and metallic oxides. Amongst inert organic adjuvants which may be used in compositions according to the invention there may be noted, for example, wood flour, cellulose fibre, starch, faecula, sugars and/or diluents which are only slight solvents such as paraffin, which can have its properties modified by the addition of organic synthetic resins and/or of salts formed by alkoylamino alkoylamines and aliphatic acids and/or aminated derivatives of montmorillonite such as bentones.

Complementary stabilisers are advantageously chosen from oxiranes, such as epoxidised oil such as epoxidised soya oil, alkoylepoxy stearates and epoxy haloalkanes or from azoic compounds or their metalliferous derivatives.

Compositions according to the present invention can also contain one or more natural or snythetic aromatic materials, one or more complementary active materials such as acaricides, insectifugal agents, bird repellants, antifungal agents, growth regulating agents, herbicides or bactericides.

So formulated, the compositions according to the present invention mahy be solid or liquid. They may be disposed on a solid porous or fibrous support. This support can be constituted for example by a paper, a felt of wool, cotton and/or synthetic fibres, or a compressed cellulose such as wood fibres, cereal fibres, alfalf- fibres and cotton fibres, felt card, a card of old papers or a card of glass fiber.

According to one valuable mode of application of the invention the solid porous or fibrous support for the composition may be lined with a permeable membrane constituting a diffusion surface and consisting, for example, of a layer of polyethylene or polypropylene or of a mixture thereof or a copolymer of ethylene and propylene or of a copolymer comprising vinylidene chloride; preferably such a membrane should be constituted by a layer of polyethylene of thickness 10–18 microns; examples of such devices are described in French Patent No. 1590647 of July 12, 1968.

Such compositions are advantageously used as insecticidal products. The presence of a body of sulphur containing material as stabiliser confers on the phosphoric ester a heightened resistance to the destructive effect of water contained in the composition and in the ambient humidity, as is shown by the following experiments which are merely given as examples. So called experiments carried out by the applicants are now set forth in order to enable a better understanding of that which has gone before.

EXPERIMENT 1

Sheet 5 × 10 cm cut from a cellulose card made by the French Company FIORONI S.A. under reference 200 were used; at the moment of use the card weighed 875 g/m$^2$.

The sheets of card were bonded in two's, back to back by means of staples; these doubled cards were divided into two series denoted 1-A and 1-B.

The doubled cards 1-A were each impregnated with 12.5 g DDVP (common name for 0,2,2-dichlorovinyl 0,0-dimethyl phosphate) and the doubled cards 1-B were each impregnated with 12.5 g of a 1% by weight solution of hydrogen sulphide in DDVP. The solution had been obtained by passing hydrogen sulphide in gaseous form into the DDVP.

The so-impregnated doubled cards were suspended in a room the temperature of which was kept at 22°± 2°C and the relative humidity of which was about 42.

At the end of 8 days the quantity of DDVP destroyed by hydrolysis was measured potentiometrically (it has been established by others that the hydrolysis of DDVP in the conditions of exposure above leads to an acid phosphoric ester and that the potentiometric value of the single acidity or of the first acidity of this ester permit the quantity of DDVP hydrolysed to be established).

The acidity present in the DDVP (1.0% equivalent DDVP) was taken into a account and this was deducted from the results obtained. Percentage quantities of DDVP decomposed by hydrolysis which were determined are expressed in the table below: the values preceded by the ± sign represent the dispersion of the results in each series

| 1-A | 1-B |
|---|---|
| 24.1 ± 2.3 | 2.0 ± 0.8 |

EXPERIMENT 2

Doubled cards were used as described in Experiment 1 but of weight 885 g/m$^2$. These cards were divided into four series called 2-A to 2-D. EAch card 2-A was impregnated with 12.5 g DDVP. The other doubled cards were impregnated each with 12.5 g of DDVP after having been impregnated with 0.25 g of one of the following salts and dried:

2-B : disodium sulphide
2-C : disodium polysulphide (d")
2-D : disodium tetrasulphide
(d") mixture of disodium trisulphide, tetrasulphide, pentasulphide and hexasulphide.

The thus impregnated cards were suspended in a room, the temperature of which was kept at 21° ± 2°C and the relative humidity of which was about 65.

At the end of 15 days the percentage quantities of DDVP destroyed were measured as noted in Experiment 1 and tabulated as follows:

| 2-A | 2-B | 2-C | 2-D |
|---|---|---|---|
| 34.2 ± 0.8 | 0.9 ± 0 | 0.5 ± 0 | 0.7 ± 0 |

The results of Experiments 1 and 2 show to what degree the DDVP is sensitive to humidity when it is not protected. They also show that hydrolysis can be reduced in substantial degree when a sulphane or a salt thereof is added to phosphoric ester.

EXPERIMENT 3

Double cards were used as described in Experiment 1 but of weight 870 g/m$^2$. These double cards were divided into two series called 3-A and 3-B. Cards 3-A were each impregnated with 12.5 g DDVP. Cards 3-B were each impregnated with 12.5 g of a 1% by weight solution of 2-mercapto pyridine in DDVP. The thus impregnated cards were suspended in a room of which the temperature was kept at 22° ± 2°C and the relative humidity of which was about 40.

At the end of 15 days the percentage quantities of DDVP destroyed were measured as noted in Experiment 1 and tabulated as follows:

| 3-A | 3-B |
|---|---|
| 36.6 ± 4.3 | 4.2 ± 0.4 |

EXPERIMENT 4

Cards of size 10 × 10 cm cut from a cellulose card made by the French company FIORONI S.A. under reference 200 were used; at the moment of use the card weighed 875 g/m$^2$.

The card squares were divided into three series of three numbered units of 4-A and 4-B; squares 4-A were each impregnated with 17 g DDVP and the other squares were each impregnated with 17 g of a 1% solution in DDVP of 2-mercaptobenzothiazole.

The so impregnated cards were suspended in a room, the temperature of which was kept at 20°±2°C and the relative humidity of which was between 55 and 60.

At the end of 15 days the percentage quantitites of DDVP destroyed were measured potentiometrically as in Experiment 1 and tabulated as follows:

| 4-A | 4-B |
|---|---|
| 31.3 ± 1.2 | 7.5 ± 0.1 |

EXPERIMENT 5

Card squares were used as described in Experiment 4 but of weight 870 g/m$^2$. These cards were divided into three series 5-A to 5-C. Cards 5-A were each impregnated with 12.5 g DDVP; the other cards were each impregnated with 12.5 g of a solution of 1,10-decanedithiol in DDVP at the following concentrations:

5-B : 1%
5-C : 2%

The thus impregnated cards were suspended in a room, the temperature of which was kept at 22° ± 2°C and the relative humidity of which was about 40.

At the end of 15 days the percentage quantities of DDVP destroyed were measured as noted in Experiment 1 and tabulated as follows:

| 5-A | 5-B | 5-C |
|---|---|---|
| 22.2 ± 1.1 | 1.6 ± 0.03 | 1.3 ± 0.1 |

EXPERIMENT 6

Squares of card were used as described in Experiment 4 but of weight 60 g/m$^2$. These cards were divided into two series called 6-A and 6-B; cards 6-A were each impregnated with 14.2 g DDVP; cards 6-B were each impregnated with 14.2 g of a 1% solution of 2-mercaptobenzimidazole in DDVP.

The so-impregnated cards were suspended in a room—the temperature of which was kept at 20° ± 2°C and the relative humidity of which was about 35.

At the end of 12 days, the percentage quantity of DDVP destroyed were measured as noted in Experiment 1 and tabulated as follows:

| 6-A | 6-B |
|---|---|
| 18.8 ± 1.0 | 3.5 ± 0.3 |

EXPERIMENT 7

Squares of cards were used as described in Experiment 4. These cards were divided into two series called 7-A and 7-B; cards 7-A were each impregnated with 17g DDVP; cards 7-B were each impregnated with 17g of a 1% solution of 2-mercaptoquinoline in DDVP.

The thus impregnated cards were suspended in a room, the temperature of which was kept at 23° ± 2°C and the relative humidity of which was between 55 and 60.

At the end of 8 days the percentage quantities of DDVP destroyed were measured as noted in Experiment 1 and tabulated as follows:

| 7-A | 7-B |
|---|---|
| 28.8 ± 2.7 | 4.0 ± 0.5 |

EXPERIMENT 8

Doubled cards were used as described in Experiment 1 but of weight 900 g/m$^2$. These cards were divided into two series 8-A and 8-B. The doubled cards 8-A were impregnated with 12.5g DDVP, while the other doubled cards were each impregnated with 12.5 g of a 3% solution of 2-mercapto-1-methylimidazole in DDVP.

The so impregnated cards were suspended in a room, the temperature of which was kept at 22° ± 2°C and the relative humidity of which was about 75.

At the end of 14 days, the percentage quantities of DDVP destroyed were measured as noted in Experiment 1 and tabulated as follows:

| 8-A | 8-B |
|---|---|
| 44.5 ± 0.5 | 9.0 ± 0.3 |

EXPERIMENT 9

Doubled cards were used as described in Experiment 1 but of weight 880 g/m$^2$. These cards were divided into five series called 9-A to 9E. Cards 9-A were each impregnated with 12.5g DDVP. The other doubled cards were each impregnated with 12.5g of a solution in DDVP at a concentration of 2–3% of one of the following compounds:

9-B : 2% 2-mercaptoethyl-2-mercapto acetate
9-C : 3% bis-(2-mercapto acetate) ethane-1,2,-diyl
9-D : 3% 1-mercapto octadecane
9-E : 3% strontium thioglycolate The so impregnated cards were suspended in a room, the temperature of which was kept at 20° ± 2°C and the relative humidity of which was about 60.

At the end of 10 days, the percentage quantitites of DDVP destroyed were measured as given in Experiment 1 and tabulated as follows:

| 9-A | 9-B | 9-C | 9-D | 9-E |
|---|---|---|---|---|
| 19.8 ± 0.3 | 0.8 ± 0.02 | 0.5 ± 0.05 | 5.7 ± 0.1 | 4.6 ± 0.4 |

The results of Experiments 3–9 show that the hydrolysis of a phosphoric ester such as DDVP can be reduced to a substantial extent when a sulphur compound chosen from organic compounds having at least one mercaptan group is added to the phosphoric ester.

EXPERIMENT 10

Doubled cards were used as described in Experiment 1 but of weight 900 g/m$^2$. These double cards were divided into seven series called 10-A to 10-F; cards 10-A were each impregnated with 12.5 g DDVP; the other cards were impregnated each with 12.5 g of a 2% solution in DDVP of one of the following compounds:
- 10-B : 2-methylthio benzimidazole
- 10-C : didecyl sulphide
- 10-D : dioctyl disulphide
- 10-E : di-2-pyridyl disulphide
- 10-F ; 1,6-dicarboxy-3,4-dithiahexane (compound commonly called 3,3'-dithiodipropionic acid)

The thus impregnated cards were suspended in a room, the temperature of which was kept at $22° \pm 2°C$ and the relative humidity of which was about 70.

At the end of 10 days the percentage quantities of DDVP destroyed were measured as given in Experiment 1 and tabulated as follows:

| 10-A | 10-B | 10-C | 10-D | 10-E | 10-F |
|---|---|---|---|---|---|
| 21.2% | 1.9 | 0 | 0 | 0 | 4.0 |
| ± 0.8% | ± 0.2 | — | — | — | ± 0.4 |

EXPERIMENT 11

Squares of card were used as described in Experiment These cards were divided into two series called 11-A and 11-B; cards 11-A were each impregnated with 12.5 g DDVP; cards 11-B were each impregnated with 12.5 g of a 1% solution in DDVP of 2-benzothiazolyl disulphide.

The so impregnated cards were suspended in a room, the temperature of which was kept at $22° \pm 2°C$ and the relative humidity of which was about 40.

At the end of 15 days, the percentage quantity of the DDVP destroyed were measured as given in Experiment 1 and tabulated as follows:

| 11-A | 11-B |
|---|---|
| 22.2 | 0 |
| ± 1.1 | — |

EXPERIMENT 12

Doubled cards were used as described in Experiment 1 but of weight 900 g/m². These cards were divided into three series 12-A to 12-C. Cards 12-A were impregnated each with 12.5 g DDVP. The other doubled cards were each impregnated with 12.5 g of a 3% solution in DDVP of one of the following compounds:
- 12-B : di-4-morpholinyl disulphide
- 12-C : 2-morpholinothio benzothiazole The thus impregnated cards were suspended in a room, the temperature of which was kept at $22 \pm 2°C$ and the relative humidity of which was about 75.

At the end of 14 days, the percentage quantities of DDVP destroyed were measured as given in Experiment 1 and tabulated as follows:

| 12-A | 12-B | 12-C |
|---|---|---|
| 44.5 | 0 | 0 |
| ± 0.5 | — | — |

EXPERIMENT 13

Doubled cards were used as described in Experiment 1 but of weight 880 g/m². These cards were divided into fifteen series called 13-A to 13-O. Cards 13-A were each impregnated with 12.5 g DDVP. The other doubled cards were each impregnated 12.5 g of a 2% solution in DDVP of one of the following compounds:
- 13-B : benzylthio benzene
- 13-C : bis(4-amino-4'-nitrophenyl) sulphide
- 13-D ; methyl-4-thiavalerianate
- 13-E : 4-methylthio-3-methylphenol
- 13-F : 4-methylthio-2-methylphenol
- 13-G : 4-methylthiophenol
- 13-H : 4-methylthio-2,6-dimethylphenol
- 13-I : bis(2-amino-4-chlorophenyl)disulphide
- 13-J : bis(4-aminophenyl) disulphide
- 13-K : dibenzyldisulphide
- 13L : bis(2-mercaptoethyl) sulphide
- 13-M : bis(2,4,5-trichlorophenyl) trisulphide
- 13N : ditertiononyl pentasulphide
- 13-O : ditertiododecyl polysulphide (d''')

(d''') mixture titrating 31.5% of sulphur containing about 20% of tetrasulphide, 70% of pentasulphide and 10% of hexasulphide of ditertiododecyl.

The thus impregnated cards were suspended in a room, the temperature of which was kept at $20° \pm 2°C$ and the relative humidity of which was about 60.

At the end of 15 days, the percentage quantities of DDVP destroyed were measured as given in Experiment 1 and tabulated as follows:

| 13-A | 13-B | 13-C | 13-D | 13-E | 13-F | 13-G | 13-H | 13-I | 13-J | 13-K | 13-L | 13-M | 13-N | 13-O |
|---|---|---|---|---|---|---|---|---|---|---|---|---|---|---|
| 19.5 | 0.5 | 1.3 | 1.9 | 0 | 0.1 | 0.3 | 0.6 | 0.6 | 0.6 | 0.2 | 4.0 | 1.3 | 0.04 | 0 |
| ± 0.3 | ± 0.03 | ± 0.02 | ± 0.3 | — | ± 0 | ± 0.01 | ± 0.02 | ± 0.01 | ± 0.4 | ± 0.01 | ± 0 | ± 0.2 | ± 0 | — |

The results of Experiments 10 to 13 show that the hydrolysis of the phosphoric ester such as DDVP can be easily controlled when a sulphur compound chosen from sulphides is added to this ester.

EXPERIMENT 14

Card squares were used as described in Experiment 4. These cards were divided into four series 14-A to 14-D. Cards 14-A were each impregnated with 12.5g of DDVP; the other cards were each impregnated with 12.5g of a 1 or 2% solution in DDVP of one of the following compounds:
- 14-B : 1% of zinc 2-mercaptobenzothiazole
- 14-C : 1% of potassium-5-mercapto-3-phenyl-2-thioxo-1-3,4-thiadiazolidine (h')
- 14-D : 2% of potassium-5-mercapto-3-phenyl-2-thioxo-1,3,4-thiadiazolidine (h')

h'. compound known under the name of bismuthiol II

The thus impregnated cards were suspended in a room, the temperature of which was kept at $22° \pm 2°C$ and the relative humidity of which was about 40.

At the end of 15 days, the percentage quantity of DDVP destroyed were measured as given in Experiment 1 and tabulated as follows:

| 14-A | 14-B | 14-C | 14-D |
|---|---|---|---|
| 22.2 ±1.1 | 0.9 ±0.06 | 2.2 ±0.6 | 1.4 ±0.02 |

EXPERIMENT 15

Squares of card were used as in Experiment 4 divided into two series 15-A and 15-B; squares 15-A were each impregnated with 17 g of DDVP and squares 15-B were each impregnated with 17g of a 1% solution in DDVP of 2 [(4-thiazolyl)methyl] benzimidazole These squares were suspended in a room, the temperature of which was kept at 23° ± 2°C and the relative humidity of which was about 57.

At the end of 7 days, the quantity of DDVP destroyed by hydrolysis was measured as in Experiment 1; the percentage quantities of DDVP thus decomposed are indicated in the following table:

| 15-A | 15-B |
|---|---|
| 28.8 ± 2.5 | 3.1 ± 0.1 |

EXPERIMENT 16

Card squares were used as in Experiment 4 which were divided into two series numbered 16A and 16-B; squares 16-A were each impregnated with 17 g of DDVP and the other squares were each impregnated with 17g of a 1% solution in DDVP of 2(4-thiazolyl)-benzimidazole.

The thus impregnated squares were suspended in a room, the temperature of which was kept at 20° ± 2°C and the relative humidity of which was about 45.

At the end of 14 days, the quantity of DDVP destroyed by hydrolysis was measured as in Experiment 1. The percentage quantities of DDVP decomposed are indicated in the following table:

| 16-A | 16-B |
|---|---|
| 27.5 ± 1.3 | 6.2 ±0.1 |

EXPERIMENT 17

Doubled cards were used as described in Experiment 1 but of weight 900 g/m². These cards were divided into two series 17-A and 17-B. The doubled cards 17-A were each imprengated with 12.5g of DDVP. The other doubled cards were each impregnated with 12.5g of a 2% solution in DDVP of 1,3,5-trithiane.

The thus impregnated cards were suspended in a room, the temperature of which was kept at 22° ± 2°C and the relative humidity of which was about 70.

At the end of 10 days, percentage quantities of DDVP destroyed were measured as given in Experiment 1 and tabulated as follows:

| 17-A | 17-B |
|---|---|
| 21.2 ± 0.8 | 0 — |

EXPERIMENT 18

Card squares were used as described in Experiment 4 but of weight 880 g/m². These cards were divided into three series 18-A to 18-C. the cards 18-A were each impregnated with 17g DDVP. The other cards were each impregnated with 17g of a 1% solution in DDVP of one of the following compounds:

18-B : 2-mercapto benzothiazole
18-C : phenothiazine

The thus impregnated cards were suspended in a room, the temperature of which was kept at 20° ± 2°C and the relative humidity of which was between 55 and 60.

At the end of 15 days, the percentage quantities of DDVP destroyed were measured as given in Experiment 1 and tabulated as follows:

| 18-A | 18-B | 18-C |
|---|---|---|
| 30.4 ± 2.2 | 4.8 ± 0.4 | 13.6 ± 0.4 |

EXPERIMENT 19

Doubled cards were used as described in Experiment 1 but of weight 885 g/m². These cards were divided into five series called 19-A to 19-E. Cards 19-A were each impregnated with 12.5g DDVP. The other doubled cards were each impregnated with 12.5g of a solution in DDVP of one of the following compounds at the concentration given:

19-B : 2% of 2-methoxyphenothiazine
19-C : 1% of 3-oxothiomorpholine
19-D : 1% of 4-oxo-2-thioxo thiazolidine
19-E : 1% of 3-methyl-4-oxo-2-thioxo thiazolidine The thus impregnated cards were suspended in a room, the temperature of which was kept at 21° ± 2°C and the relative humidity of which was about 65.

At the end of 15 days, the percentage quantities of DDVP destroyed were measured as given in Experiment 1 and tabulated as follows:

| 19-A | 19-B | 19-C | 19-D | 19-E |
|---|---|---|---|---|
| 34.2 ± 0.8 | 0.7 ± 0.04 | 0.06 ± 0 | 1.7 ± 0.06 | 0.3 ± 0 |

EXPERIMENT 20

Doubled cards were used as described in Experiment 1 but of weight 900 g/m². These cards were divided into three series denoted 20-A to 20-C. Cards 20-A were each impregnated with 12.5g DDVP. The other doubled cards were each impregnated with 12.5g of a solution at 2% in DDVP of one of the following compounds:

20-B : 2-cyclohexylaminothio benzithiazole
20-C : 3-methyl-2-oxobenzothiazoline

The thus impregnated cards were suspended in a room, the temperature of which was kept at 22° ± 2° C and of which the relative humidity was between 70 and 75.

At the end of 15 days, the percentage quantities of DDVP destroyed were measured as given in Experiment 1 and tabulated as follows:

| 20-A | 20-B | 20-C |
| --- | --- | --- |
| 41.3 | 0 | 2.2 |
| ± 1.1 | — | ± 0.3 |

| 23-A | 23-B | 23-C |
| --- | --- | --- |
| 36.8 | 4.3 | 0 |
| ± 2.4 | ± 0.8 | — |

EXPERIMENT 21

Card squares were used as described in Experiment 4 but of weight 870 g/m². These cards were divided into two series 21-A and 21-B. Cards 21-A were each impregnated with 17g DDVP. Cards 21-B were each impregnated with 17g of a 1% solution in DDVP of 3-phenyl-1,3,4-thiazolidine-2,5-dithione.

The thus impregnated cards were suspended in a room, the temperature of which was kept at 22° ± 2°C and the relative humidity of which was about 65.

At the end of 8 days the percentage quantities of DDVP destroyed were measured as given in Experiment 1 and tabulated as follows:

| 21-A | 21-B |
| --- | --- |
| 35.3 | 3.9 |
| ± 1.6 | ± 0.3 |

The results of Experiments 14 to 21 show that the hydrolysis of the phosphoric ester such as DDVP can be reduced in substantial proportion when a sulphur compound chosen from heterocyclic compounds is added to this ester.

EXPERIMENT 22

Card squares were used as described in Experiment 4; these cards were divided into two series 22-A and 22-B; cards 22-A were each impregnated with 15g DDVP; cards 22-B were each impregnated with 15g of a 1% solution of thiobenzoic acid in DDVP.

The thus impregnated cards were suspended in a room, the temperature of which was kept at 23° ± 2°C and of which the relative humidity was about 60.

At the end of 8 days, the percentage quantities of DDVP destroyed were measured as given in Experiment 1 and tabulated as follows:

| 22-A | 22-B |
| --- | --- |
| 35.3 | 12.0 |
| ±1.6 | ±0.2 |

EXPERIMENT 23

Doubled cards were used as described in Experiment 1 but of weight 895 g/m². These cards were divided into three series 23-A to 23-C. Cards 23-A were each impregnated with 12.5g DDVP; the other doubled cards were each impregnated with 12.5 g of a 1.5% solution in DDVP of one of the following compounds:

23-B : methylbutylxanthate
23-C : bis(ethoxycarbonyl) disulphide

The thus impregnated cards were suspended in a room, the temperature of which was kept at 22° ± 2°C and the relative humidity of which was about 70.

At the end of 15 days, the percentage quantities of DDVP destroyed were measured as given in Experiment 1 and tabulated as follows:

EXPERIMENT 24

Card squares were used as described in Experiment 4. These cards were divided into three series 24-A to 24-C. Cards 24-A were each impregnated with 12.5 g of DDVP; the other cards were each impregnated with 12.5 g of a solution at one or two percent in DDVP of one of the following compounds:

24-B : 1% of potassium butyl trithiocarbonate
24-C: 2% of potassium butyl trithiocarbonate The thus impregnated cards were suspended in a room, the temperature of which was kept at 22° ± 2°C and of which the relative humidity was about 40.

At the end of 15 days, the percentage quantities of DDVP destroyed were measured as given in Experiment 1 and tabulated as follows:

| 24-A | 24-B | 24-C |
| --- | --- | --- |
| 22.2 | 2.2 | 1.7 |
| ± 1.1 | ± 0.4 | ± 0.03 |

EXPERIMENT 25

Doubled cards were used as described in Experiment 1 but of weight 900 g/m². These cards were divided into two series 25-A and 25-B. Cards 25-A were each impregnated with 12.5g of DDVP. The other doubled cards were each impregnated with 12.5g. of a 2% solution in DDVP of zinc isopropyl xanthate.

The thus impregnated cards were suspended in a room, the temperature of which was kept at 22° ± 2°C, and the relative humidity of which was about 75.

At the end of 15 days, the percentage quantities of DDVP destroyed were measured as given in Experiment 1 and tabulated as follows:

| 25-A | 25-B |
| --- | --- |
| 41.3 | 0.04 |
| ±0.6 | ±0 |

EXPERIMENT 26

Doubled cards were used as described in Experiment 1 but of weight 880 g/m². These cards were divided into seven series called 26-A to 26-G. Cards 26-A were each impregnated with 12.5g. of DDVP. The other doubled cards were each impregnated with 12.5g. of a 2 or 3% solution in DDVP of one of the following compounds:

26-B : 2% of bis(carboxymethyl) trithiocarbonate
26-C : 3% of dibenzyltrithiocarbonate
26-D : 3% of ethylene trithiocarbonate
26-E : 3% of isopropylthiocarbonyldisulphide
26-F : 3% of potassium thioacetate
26-G : 3% of zincthiobenzoate The thus impregnated cards were suspended in a room, the temperature of which was kept at 20° ± 2°C and the relative humidity of which was 60.

At the end of 10 days, the percentage quantities of DDVP destroyed were measured as given in Experiment 1 and tabulated as follows:

| 26-A | 26-B | 26-C | 26-D | 26-E | 26-F | 26-G |
|------|------|------|------|------|------|------|
| 19.8 ± 0.3 | 8.9 ± 0.1 | 0 — | 0 — | 0 — | 0 — | 0.5 ± 0.02 |

The results of experiments 22 to 26 show that the hydrolysis of a phosphoric ester such as DDVP can be reduced in notable proportion when a sulphur compound chosen from thioic compounds or salts thereof is added to this ester.

EXPERIMENT 27

Card squares were used as described in Experiment 4 but of weight 870 g/m². These cards were divided into three series called 27-A, 27-B and 27-C. Cards 27-A were each impregnated with 17 g DDVP; the other cards were each impregnated with 17g of a 1% solution in DDVP of one of the following compounds:
27-B : thiobenzamide
27-C : thionicotinamide The thus impregnated cards were suspended in a room, the temperature of which was kept at 23° ± 2°C and the relative humidity of which was about 60.

At the end of 8 days the percentage quantities of DDVP destroyed were measured as given in Experiment 1 and tabulated as follows:

| 27-A | 27-B | 27-C |
|------|------|------|
| 35.3 ± 1.6 | 3.4 ± 1.0 | 0 — |

EXPERIMENT 28

Doubled cards were used as described in Experiment 1. These cards were divided into two series 28-A and 28-B. Cards 28-A were each impregnated with 14g DDVP; card 28-B were each impregnated with 14g of a 1% solution of thioacetamide in DDVP.

The thus impregnated cards were suspended in a room, the temperature of which was kept at 22° ± 2°C and the relative humidity of which was about 45.

At the end of 8 days, the percentage quantities of DDVP destroyed were measured as given in Experiment 1 and tabulated as follows:

| 28-A | 28-B |
|------|------|
| 28.7 ± 1.0 | 0.5 ± 0.05 |

EXPERIMENT 29

Card squares were used as described in Experiment 4. These cards were divided into two series 29-A and 29-B. Cards 29-A were each impregnated with 12.5g of DDVP; cards 29-B were each impregnated with 12.5g. of a 1% solution in DDVP of 2,6-dichloro thiobenzamide (a compound known under the common name of "chlorthiamide").

The thus impregnated cards were suspended in a room, the temperature of which was kept at 22° ± 2°C and the relative humidity of which was about 40.

At the end of 15 days, the percentage quantities of DDVP destroyed were measured as given in Experiment 1 and tabulated as follows:

| 29-A | 29-B |
|------|------|
| 22.2 ± 1.1 | 1.0 ± 0.1 |

EXPERIMENT 30

Doubled cards were used as described in Experiment 1 but of weight 900 g/m². These cards were divided into three series 30-A to 30-C. Cards 30-A were each impregnated with 12.5g of DDVP. The other doubled cards were each impregnated with 12.5 g of a 0.5 and 1% solution in DDVP of thioisonicotinamide.
30-B : 0.5% of thioisonicotinamide
30-C : 1% of thioisonicotinamide The thus impregnated cards were suspended in a room, the temperature of which was kept at 22° ± 2°C and the relative humidity of which was about 75.

At the end of 20 days, percentage quantities of DDVP destroyed were measured as given in Experiment 1 and tabulated as follows:

| 30-A | 30-B | 30-C |
|------|------|------|
| 56.5 ± 0.3 | 0.5 ± 0.02 | 0.4 ± 0.02 |

EXPERIMENT 31

Doubled cards were used as described in Experiment 1 but of weight 880 g/m². These cards were divided into three series 31-A to 31-C. Cards 31-A were each impregnated with 12.5 g of DDVP. The other doubled cards were each impregnated with 12.5 g of a 3% solution in DDVP of one of the following compounds:
31-B : epsilon thiocaprolactam
31-C : dithiooxamide The thus impregnated cards were suspended in a room, the temperature of which was kept at 20° ± 2°C and the relative humidity of which was about 60.

At the end of 10 days, the percentage quantities of DDVP destroyed were measured as given in Experiment 1 and tabulated as follows:

| 31-A | 31-B | 31-C |
|------|------|------|
| 19.8 ± 0.3 | 7.9 ± 0.5 | 0.4 ± 0.03 |

The results of Experiments 27 to 31 show that the hydrolysis of a phosphoric ester such as DDVP can be reduced by substantial proportion when a sulphur compound chosen from thiamides is added to this ester.

EXPERIMENT 32

Card squares were used as described in Experiment 4. These cards were divided into seven series 32-A to 32-G. Cards 32-A were each impregnated with 12.5 g of DDVP; the other cards were each impregnated with 12.5 g of a solution in DDVP of one of the following compounds at the concentration given:
32-B : 1% of methyl N,N-diethyldithiocarbamate
32-C : 1% of ethyl N,N-diethyldithiocarbamate 32-D : 1% of methyl N,N-dibutyldithiocarbamate
32-E : 2% of methyl N,N-dibutyldithiocarbamate
32-F : 1% of methyl N,N-pentamethylene dithiocarbamate
32-G : 2% of methyl N,N-pentamethylene dithiocarbamate The thus impregnated cards were suspended in a room, the temperature of which was kept at 22° ± 2°C and the relative humidity of which was about 65.

At the end of 15 days, percentage quantities of DDVP destroyed were measured as given in Experiment 1 and tabulated as follows:

| 32-A | 32-B | 32-C | 32-D | 32-E | 32-F | 32-G |
|------|------|------|------|------|------|------|
| 29.9 | 0.6  | 0.3  | 0.7  | 0.6  | 0.7  | 0.2  |
| ± 1.4 | ± 0.05 | ± 0.02 | ± 0.1 | ± 0.03 | ± 0.00 | ± 0.01 |

EXPERIMENT 33

Double cards were used as those described in Experiment 1 but of weight 890 g/m². These doubled cards were divided into two series 33-A and 33-B; double cards 33-A were each impregnated with 12.5 g of DDVP; the other doubled cards were each impregnated with 12.5 g. of a solution in DDVP at 2% of zinc N,N-dibutyldithiocarbamate.

The thus impregnated cards were suspended in a room, the temperature of which was kept at 22° ± 2°C and the relative humidity of which was about 75.

At the end of 15 days, the percentage quantities of DDVP destroyed were measured as given in Experiment 1 and tabulated as follows:

| 33-A  | 33-B  |
|-------|-------|
| 41.3  | 0.4   |
| ± 0.6 | ± 0.07 |

EXPERIMENT 34

Card squares were used as those described in Experiment 4. These cards were divided into three series 34-A to 34-C; cards 34-A were each impregnated with 12.5 g of DDVP; the other cards were impregnated with 12.5g of a solution in DDVP of one of the following compounds at the concentration of 1%:
34-B: zinc N,N-dimethyl dithiocarbamate (h)
34-C: zinc N,N-diethyl dithiocarbamate
h. compound known under the common name of "zirame".

The thus impregnated cards were suspended in a room, the temperature of which was kept at 22° ± 2°C and the relative humidity of which was about 40.

At the end of 15 days the percentage quantity of DDVP destroyed were measured as given in Experiment 1 and tabulated as follows:

| 34-A | 34-B | 34-C |
|------|------|------|
| 22.2 | 0    | 0    |
| ± 1.1 | —   | —    |

EXPERIMENT 35

Squares of card were used as described in Experiment 4. These cards were divided into ten series denoted 35-A to 35-J; cards 35-A were each impregnated with 12.5 g DDVP; the other cards were each impregnated with 12.5g of a solution in DDVP of one of the following compounds at the concentration given:
35-B: 1% of zinc N,N-diethyldithiocarbamate
35-C: 2% of zinc N,N-diethyldithiocarbamate
35-D: 0.5% of cadmium N,N-diethyldithiocarbamate
35-E: 1% of cadmium N,N-diethyldithiocarbamate
35-F: 0.05% of ferric N,N-diethyldithiocarbamate
35-G: 0.3% of cupric N,N-diethyldithiocarbamate
35-H: 0.05% of silver N,N-diethyldithiocarbamate
35-I: 1% of zinc N-ethyl-N-phenyldithiocarbamate
35-J: 2% of zinc N-ethyl-N-phenyldithiocarbamate The thus impregnated cards were suspended in a room, the temperature of which was kept at 22° ± 2°C and the relative humidity of which was about 65.

At the end of 15 days, the percentage quantities of DDVP destroyed were measured as given in Experiment 1 and tabulated as follows:

| 35-A | 35-B | 35-C | 35-D | 35-E | 35-F | 35-G | 35-H | 35-I | 35-J |
|------|------|------|------|------|------|------|------|------|------|
| 29.9 | 0.3  | 0    | 1.0  | 0.8  | 0    | 0.9  | 0.2  | 0.1  | 0    |
| ± 1.4 | ± 0.06 | — | ± 0.15 | ± 0.04 | — | ± 0.06 | ± 0.01 | ± 0.01 | — |

EXPERIMENT 36

Doubled cards were used as described in Experiment 1. These doubled cards were divided into three series 36-A to 36-C; cards 36-A were each impregnated with 12.5g DDVP; the other cards were each impregnated with 12.5g of a solution in DDVP of one of the following compounds at the concentration given:
36-B: 1% of zinc N,N-dimethyldithiocarbamate (h)
36-C: 0.1% of zinc N,N'-ethylene bis(dithiocarbamate) (h")
h". compound known under the common name of zinebe.

The thus impregnated cards were suspended in a room, the temperature of which was kept at 22° ± 2°C and the relative humidity of which was about 45.

At the end of 8 days the precentage quantities of DDVP destroyed were measured as given in Experiment 1 and tabulated as follows:

| 36-A  | 36-B   | 36-C  |
|-------|--------|-------|
| 31.2  | 1.3    | 1.2   |
| ± 1.9 | ± 0.15 | ± 0.2 |

EXPERIMENT 37

Doubled cards were used as described in Experiment 1 but of weight 885 g/m². These cards were divided into ten series 37-A to 37-J. Cards 37-A were each impregnated with 12.5g DDVP; the other doubled cards were each impregnated with 12.5g of a 1% solution in DDVP of one of the folloing compounds:

37-B: zince N,N-dibenzyl dithiocarbamate
37-C: sodium N,N-dibutyl dithiocarbamate
37-D: sodium N,N-diethyl dithiocarbamate
37-E: zinc N,N-diamyl dithiocarbamate
37-F: bismuth N,N-dimethyl dithiocarbamate
37-G: dibutylamine N,N-dibutyl dithiocarbamate
37-H: nickel N,N-pentamethylene dithiocarbamate
37-I: pyridine N,N-pentamethylene dithiocarbamate
37-J: lead N,N-pentamethylene dithiocarbamate The thus impregnated cards were suspended in a room, the temperature of which was kept at 21° ± 2°C and the relative humidity of which was about 65.

At the end of 15 days, the percentage quantities of DDVP destroyed were measured as given in Experiment 1 and tabulated as follows:

| 37-A | 37-B | 37-C | 37-D | 37-E | 37-F | 37-G | 37-H | 37-I | 37-J |
| --- | --- | --- | --- | --- | --- | --- | --- | --- | --- |
| 34.2 | 0 | 0.3 | 0.06 | 0 | 0.5 | 0.5 | 0.3 | 0 | 0.6 |
| ± 0.8 | — | ± 0.01 | ± 0 | — | ± 0.03 | ± 0.06 | ± 0 | — | ± 0.07 |

The results of experiments 32 to 37 show that the hydrolysis of a phosphoric ester such as DDVP can be reduced by a very great degree when a dithiocarbamic sulphur compound is added thereto; the results of experiment 35 show furthermore that it is possible to obtain a very good stabilisation by using certain compounds of sulphur at a concentration as weak as 0.05%.

EXPERIMENT 38

Doubled cards were used as described in Experiment 1 but of weight 890 g/m². These cards were divided into two series 38-A and 38-B: Cards 38-A were each impregnated with 12.5 g DDVP. The other doubled cards were each imregnated with 12.5 g. of a 3% solution in DDVP of 2,4-bis(butylthiocarboxamido)toluene. The thus impregnated cards were suspended in a room, the temperature of which was kept at 22° ± 2°C and of which the relative humidity was about 75.

At the end of 15 days the percentage quantity of DDVP destroyed were measured as is given in Experiment 1 and tabulated as follows:

| 38-A | 38-B |
| --- | --- |
| 41.3 | 4.1 |
| ± 0.6 | ± 0.8 |

EXPERIMENT 39

Card squares were used as described in Experiment 4 but of weight 860 g/m². These cards were divided into two series 39-A and 39-B. Cards 39-A were impregnated each with 17G DDVP; The other cards were impregnated each with 17G of a 1% solution in DDVP of 2[N(3-chlorophenyl)carbamoylthio] benzimidazole.

The thus impregnated cards were suspended in a room, the temperature of which was kept at 20° ± 2°C and the relative humidity of which was about 45.

At the end of 14 days, the percentage quantities of DDVP destroyed were measured as in Experiment 1 and tabulated as follows:

| 39-A | 39-B |
| --- | --- |
| 27.5 | 9.3 |
| ± 1.3 | ± 1.0 |

The results of experiments 38 and 39 shows that the hydrolysis of a phosphoric ester such as DDVP can be reduced to a very great degree when a sulphur compound chosen from thiocarbamic esters is added to this phorphoric ester.

EXPERIMENT 40

Squares of card were used as described in Experiment 4. These cards were divided into three series 40-A to 40-C; cards 40-A were each impregnated with 12.5g DDVP; the other cards were each impregnated with 12.5g of a solution in DDVP of the following compounds at the following proportions:

40-B: 1% of bis(N,N-diethylthiocarbamoyl) disulphide
40-C: 2% of bis(N,N-diethylthiocarbamoyl) disulphide This compound is commonly called tetraethylthiuramdisulphide.

The this impregnated cards were suspended in a room, of which the temperature was kept at 22° ± 2°C and of which the relative humidity was about 65.

At the end of 15 days the percentage quantity of DDVP destroyed were measured as given in Experiment 1 and tabulated as follows:

| 40-A | 40-B | 40-C |
| --- | --- | --- |
| 29.9 | 0.7 | 0.4 |
| ± 1.4 | ± 0.1 | ± 0.1 |

EXPERIMENT 41

Card squares were used as described in Experiment 4. These cards were divided into three series 41-A to 41-C; cards 41-A were each impregnated with 12.5 g DDVP; the other cards were each impregnated with 12.5g of a 1% solution in DDVP of one of the following compounds:

41-B: bis(N,N-dimethylthiocarbamoyl) sulphide (g')
41-C: bis(N,N-dimethylthiocarbamoyl) disulphide (g")

g'. compound commonly called tetramethylthiuram monosulphide
g". compound commonly called tetramethylthiuram disulphide and known under the common name of thirame.

The thus impregnated cards were hung up in a room, the temperature of which was kept at 22° ± 2°C and the relative humidity of which was about 40.

At the end of 15 days the percentage quantity of DDVP destroyed were measured as given in Experiment 1 and tabulated as follows:

| 41-A | 41-B | 41-C |
|---|---|---|
| 22.2 ± 1.1 | 0 — | 0 — |

EXPERIMENT 42

Doubled cards were used as described in Experiment 1 but of weight 885 g/m². These cards were divided into seven series 42-A to 42-G. Cards 42-A were each impregnated with 12.5g DDVP; the other doubled cards were each impregnated with 12.5g of a 1% solution in DDVP of one of the following compounds:
42-B: bis(piperidinocarbothioyl) tetrasulphide
42-C: bis(N,N-diethylthiocarbamoyl) disulphide
42-D: bis(N,N-dibutylthiocarbamoyl) disulphide
42-E: bis(N,N-pentamethylenethiocarbamoyl) sulphide
42-F: bis(N,N-pentamethylenethiocarbamoyl) disulphide
42G: bis(N,N-pentamethylenethiocarbamoyl) tetrasulphide The thus impregnated cards were suspended in a room, the temperature of which was kept at 21° ± 2°C and of which the relative humidity was about 65.

At the end of 15 days, percentage quantities of DDVP destroyed were measured as given in Experiment 1 and tabulated as follows:

| 42-A | 42-B | 42-C | 42-D | 42-E | 42-F | 42-G |
|---|---|---|---|---|---|---|
| 34.2 ± 0.8 | 0 — | 0.03 ± 0 | 0.06 ± 0.01 | 0.06 ± 0.01 | 0 — | 0 — |

The results of Experiments 40 to 42 show that the hydrolysis of the phosphoric ester such as DDVP can be reduced in substantial proportion when a thiuram compound of sulphur is added to the ester.

EXPERIMENT 43

Doubled cards were used as described in Experiment 1 but of weight 900 g/m². These doubled cards were divided into three series 43-A to 43-C; the doubled cards 43-A were each impregnated with 12.5g DDVP; the other doubled cards were each impregnated with 12.5g of a 1.5% solution in DDVP of one of the following compounds:
43-B: methylisothiocyanate
43-C: ethylisothiocyanate The thus impregnated doubled cards were suspended in a room, the temperature of which was kept at 22° ± 2°C and of which the relative humidity was about 75.

At the end of 15 days the percentage quantities of DDVP destroyed were measured as given in Experiment 1 and tabulated as follows:

| 43-A | 43-B | 43-C |
|---|---|---|
| 41.3 ± 0.6 | 12.5 ± 2.4 | 6.3 ± 0.7 |

The results of this experiment show that the hydrolysis of the phosphoric ester such as DDVP can be reduced in substantial proportions when a sulphur compound selected from isothiocyanic esters is added to the this ester.

EXPERIMENT 44

Card squares were used as described in Experiment 4 but of weight 870 g/m². These cards were divided into five series 44-A to 44-E; cards 44-A were each impregnated with 17G DDVP; the other cards were each impregnated with 17g of a 1% solution in DDVP of one of the following compounds:
44-B: thiourea
44-C: N,N'-dimethylthiourea
44-D: N,N'-diethylthiourea
44-E: ethylene thiourea The thus impregnated cards were suspended in a room, of which the temperature was kept at 20° ± 2°C and of which the relative humidity was between 55 and 60.

At the end of 15 days, the percentage quantities of the DDVP destroyed were measured as given in Experiment 1 and tabulated as follows:

| 44-A | 44-B | 44-C | 44-D | 44-E |
|---|---|---|---|---|
| 25.8 ± 1.3 | 5.5 ± 0.2 | 8.7 ± 0.4 | 16.8 ± 1.2 | 6.4 ± 0.4 |

EXPERIMENT 45

Card squares were used as described in Experiment but the weight of which was 885 g/m². These cards were divided into four series 45-A to 45-D; cards 45-A were each impregnated with 17G DDVP; the other cards were each impregnated with 17g of a 1% solution in DDVP of one of the following compounds:
45-B: N-methylthiourea
45-C: N-allylthiourea (c)
45-D: N,N,N',N'-tetramethylthiourea
c. compound also known under the common name of thiosinamine.

The thus impregnated cards were suspended in a room, the temperature of which was kept at 22° ± 2°C and the relative humidity of which was about 65.

At the end of 8 days the percentage quantities of DDVP destroyed were measured as given in Experiment 1 and tabulated as follows:

| 45-A | 45-B | 45-C | 45-D |
|---|---|---|---|
| 35.3 ± 2.7 | 3.1 ± 0.2 | 3.4 ± 0.3 | 21.9 ± 1.4 |

EXPERIMENT 46

Doubled cards were used as described in Experiment 1 but of weight 885 g/m². These cards were divided into two series called 46-A and 46-B. Cards 46-A were each impregnated with 12.5g DDVP. The other cards were each impregnated with 12.5g of a 1% solution in DDVP of 1,2-bis(N'-ethoxycarbonylthiourido) benzene.

The thus impregnated cards were suspended in a room, the temperature of which was kept at 21° ± 2°C and the relative humidity of which was about 65.

At the end of 15 days, the percentage quantities of DDVP destroyed were measured as given in Experiment 1 and tabulated as follows:

| 46-A | 46-B |
|---|---|
| 34.2 | 0.3 |

-continued

| 46-A | 46-B |
|---|---|
| ± 0.8 | ± 0.1 |

The results of Experiments 43 to 46 show that the hydrolysis of a phosphoric ester such as DDVP can be reduced in notable proportions when a sulphur compound chosen from thioureas is added to this ester.

EXPERIMENT 47

Doubled cards were used as described in Experiment 1 but of weight 880 g/m². These cards were divided into two series 47-A or 47-B. Cards 47-A were each impregnated with 12.5 g DDVP. The other doubled cards were each impregnated with 12.5 g of a 2% solution in DDVP of 2-methyl thiirane.

The thus impregnated cards were suspended in a room, the temperature of which was kept at 20° ± 2°C and the relative humidity of which was about 60.

At the end of 10 days, the percentage quantities of DDVP destroyed were measured as given in Experiment 1 and tabulated as follows:

| 47-A | 47-B |
|---|---|
| 19.8 ± 6.3 | 0 — |

EXPERIMENT 48

Doubled cards were used as described in Experiment 1 but of weight 895 g/m². These cards were divided into three series 48-A to 48-C; the doubled cards 48-A were each impregnated with 12.5g of DDVP; the other doubled cards were each impregnated with 12.5g of a 1.5% solution in DDVP of one of the following compounds:
 48-B : 2-ethyl thiirane
 48-C : 2-chloromethyl thiirane The thus impregnated cards were suspended in a room, the temperature of which was kept at 22° ± 2°C and the relative humidity of which was about 70.

At the end of 15 days, the percentage quantities of DDVP destroyed were measured as given in Experiment 1 and tabulated as follows:

| 48-A | 48-B | 48-C |
|---|---|---|
| 33.8 ± 4.1 | 0 — | 0 — |

This experiment shows the particularly remarkable results which can be obtained in the stabilisation of phosphoric esters such as DDVP when a sulphur compound chosen from thiiranes is added thereto.

EXPERIMENT 49

Doubled cards were used as described in Experiment 1 but of weight 900 g/m². These double cards are divided into four series 49-A to 49-D; cards 49-A were each impregnated with 12.5g DDVP, the other cards being each impregnated with 12.5g of a solution in DDVP of one of the following compounds at the concentration given:
 49-B : 1.5% of N-trichloromethylthiophthalimide (f)
 49-C : 1.5% of N-trichloromethylthiotetrahydrophthalimide (f')
 f. compound known under the common name of "folpet"
 f'. compound known under the common name of "captane"

The thus impregnated cards were suspended in a room, the temperature of which was kept at 22° ± 2°C and the relative humidity of which was about 75.

At the end of 15 days, the percentage quantities of DDVP destroyed were measured as given in Experiment 1 and tabulated as follows:

| 49-A | 49-B | 49-C |
|---|---|---|
| 41.3 ± 0.6 | 4.2 ± 0.2 | 10.7 ± 2.1 |

The results of this Experiment show the hydrolysis of a phosphoric ester such as DDVP can be reduced in notable proportion when a sulphur compound chosen from sulphenamides is added thereto.

EXPERIMENT 50

Doubled cards were used as described in Experiment 1 but of weight 900 g/m². These cards were divided into four series 50-A to 50-D. Cards 50-A were each impregnated with 12.5g of DDVP. The other doubled cards were each impregnated with 12.5g of a 3% solution in DDVP of one of the following compounds:
 50-B : 8-quinolyltrichloromethane sulphanate
 50-C : 4-methoxy-3-tertiobutylphenyltrichloromethane sulphenate
 50-D : 3,5,-dimethoxyphenyltrichloromethane sulphenate The thus impregnated cards were suspended in a room, the temperature of which was kept at 22° ± 2°C and of which the relative humidity was about 75.

At the end of 10 days, the percentage quantities of DDVP destroyed were measured as given in Experiment 1 and tabulated as follows:

| 50-A | 50-B | 50-C | 50-D |
|---|---|---|---|
| 36.8 ± 0.9 | 6.6 — | 1.8 — | 1.0 — |

The results of this experiment show that the hydrolysis of a phosphoric ester such as DDVP can be reduced in notable proportions when a sulphur compound selected from sulphenic esters is added to this ester.

EXPERIMENT 51

Doubled cards were used as described in Experiment 1 but of weight 890 g/m². These doubled cards were divided into two series 51-A and 51-B; cards 51-A were each impregnated with 12.5g of DDVP; the other double cards were each impregnated with 12.5g of a 2% solution in DDVP of 4,4'-dimethoxythiobenzophenone.

The thus impregnated cards were suspended in a room, the temperature of which was kept at 22° ± 2°C and the relative humidity of which was about 70.

At the end of 15 days, the percentage quantities of DDVP destroyed were measured as given in Experiment 1 and tabulated as follows:

| 51-A | 51-B |
|---|---|
| 41.1 | 3.0 |

| 51-A | 51-B |
|---|---|
| ± 0.8 | ± 0.7 |

The results of this Experiment show that the hydrolysis of a phosphoric ester such as DDVP can be reduced in substantial proportion when a sulphur compound chosen from thio ketones is added thereto.

EXPERIMENT 52

Cards of size 5 × 10 cm were used as described in Experiment 1 but left at a single thickness. These cards were divided into three series 52-A to 52-C. Cards 52-A were each impregnated with 6g of 0(2,2-dibromovinyl)0,0-dimethylphosphate. The other cards were each impregnated with 6g of a solution of one of the following compounds at 2% in 0(2,2dibromovinyl)0,0-dimethyl phosphate:

52-B : 2(cyclohexylaminothio) benzothiazole
52-C : zinc N,N-diethyldithiocarbamate The thus impregnated cards were suspended in a room, the temperature of which was kept at 22° ± 2°C and the relative humidity of which was about 60.

At the end of 16 days, the percentage quantities of ester destroyed were measured potentiometrically. Account was taken of the starting acidity present in the phosphoric ester (equivalent to 7.4% of the ester) and this was deducted from the results.

| 52-A | 52-B | 52-C |
|---|---|---|
| 14.8 | 8.0 | 2.8 |

EXPERIMENT 53

Card squares of size 5 × 10 cm as those described in Experiment 1 were used but left at a single thickness. These cards were divided into five series called 53-A to 53-B. Cards 53-A were each impregnated with 6g of 0(2,2-dichlorovinyl)0,0-diethyl phosphate. The other single cards were each impregnated with 6g of a solution of one of the following compounds at 2% in 0(2,2-dichlorovinyl)0,0-diethyl phosphate:

53-B : 2(cyclohexylaminothio) benzothiazole
53-C : zinc N,N-diethyldithio carbamate
53-D : bis(2-benzothiazolyl)disulphide
53-E : bis(N,N-dimethylthiocarbamoyl) disulphide (g″)

The thus impregnated cards were suspended in a room, the temperature of which was kept at 22° ± 2°C and the relative humidity of which was about 60.

At the end of 48 days, the percentage quantities of DDVP destroyed were measured as given in Experiment 1 and tabulated as follows:

| 53-A | 53-B | 53-C | 53-D | 53-E |
|---|---|---|---|---|
| 7.1 | 2.5 | 0 | 2.7 | 1.9 |

EXPERIMENT 54

Doubled cards were used as described in Experiment 1 but of weight 885 g/m². These cards were divided into four series 54-A to 54-D. Cards 54-A were each impregnated with 14g DDVP. The other double cards were each impregnated with 14g of a solution in DDVP of one of the following compounds:

54-B : 1% of 2 [(4-thiazolyl) methyl]benzimidazole
54-C : 1% of azobenzene
54-D : 0.5% of 2 [(4-thiazolyl) methyl]benzimidazole + 0.5% of azobenzene The thus impregnated cards were suspended in a room, the temperature of which was kept at 22° ± 2°C and the relative humidity of which was about 65.

At the end of 12 days, the percentage quantities of DDVP destroyed were measured as given in Experiment 1 and tabulated as follows:

| 54-A | 54-B | 54-C | 54-D |
|---|---|---|---|
| 46.5 | 10.7 | 19.1 | 7.3 |

EXPERIMENT 55

Doubled cards were used as described in Experiment 1. These doubled cards were divided into five series 55-A to 55-B. Cards 55-A were each impregnated with 12.5 g DDVP; the other cards were each impregnated with 12.5 g of a solution in DDVP as follows:

55-B : 1% of thioacetamide
55-C : 1% of azobenzene
55-D : 0.33% thioacetamide + 0.66% azobenzene
55-E : 0.5% thioacetamide + 0.5% azobenzene After impregnation the double cards were each placed in a sachet formed by a mesh of nylon 66 made from 0.14 mm thread and formed into a 0.3mm mesh made by the French company Tripette et Renaud. The devices thus prepared were suspended in a room, the temperature of which was kept at 22° ± 2°C and the relative humidity of which was about 40. At the end of 15 days, the percentage quantities of the DDVP destroyed were measured as given in Experiment 1 and tabulated as follows.

| 55-A | 55-B | 55-C | 55-D | 55-E |
|---|---|---|---|---|
| 38.1 | 0.6 | 3.5 | 0.15 | 0 |
| ± 0.6 | ± 0.1 | ± 0.8 | ± 0.02 | — |

EXPERIMENT 56

Doubled in sachet cards were used as described in Experiment 55. The doubled cards were divided into six series 56-A to 56-F. The cards 56-A were each impregnated with 12.5g DDVP; the other doubled cards were each impregnated with 12.5g of a solution in DDVP as follows:

56-B : 1% of 2-mercaptobenzothiazole
56-C : 1% of 4-diethylaminoazobenzene
56-D : 0.5% of 2-mercaptobenzothiazole + 0.5% 4-diethylaminoazobenzene
56-E : 1% of 1-phenylazo-2-naphthol
56-F : 0.5% of 2-mercaptobenzothiazole + 0.5% 4-diethylaminoazobenzene The thus impregnated cards were suspended in a room, the temperature of which was kept at 22° ± 2°C and the relative humidity of which was about 35.

At the end of 30 days, the percentage quantities of DDVP destroyed, were measured as given in Experiment 1 and tabulated as follows:

| 56-A | 56-B | 56-C | 56-D | 56-E | 56-F |
|---|---|---|---|---|---|
| 44.6 ± 1.0 | 4.5 ± 0.4 | 3.6 ± 0.5 | 3.5 ± 0.5 | 12.9 ± 2.0 | 3.8 ± 0.4 |

EXPERIMENT 57

Doubled cards in sachets were used as described in Experiment 55 but in which the weight of the card was 900 g/m². The double cards were divided into eight series 57-A to 57-H; cards 57-A were each impregnated with 12.5g DDVP; the other double cards were each impregnated with 12.5g of a solution in DDVP as follows:
- 57-B : 1.75% of bis(N,N-dimethylthiocarbamoyl) disulphide
- 57-C : 1.75% of 4-phenylazo-3-methyl-1-phenyl-5-hydroxypyrazole
- 57-D : 1.25% of bis(N,N-dimethylthiocarbamoyl) disulphide + 0.5% 4-phenylazo-3-methyl-1-phenyl-5-hydroxypyrazole
- 57-E : 1.75% of 4-diethylaminoazobenzene
- 57-F : 1.25% of bis(N,N-dimethylthiocarbamoyl) disulphide + 0.5% of 4-diethylaminoazobenzene
- 57-G : 1.50% of 1-phenylazo-2-naphthyl
- 57-H : 1.25% of bis(N,N-dimethylthiocarbamoyl) disulphide + 0.25% 1-phenylazo-2-naphthol The thus impregnated cards were suspended in a room, the temperature of which was kept at 22° ± 2°C and the relative humidity of which was about 70.

At the end of 30 days, the percentage quantities of DDVF destroyed were measured as given in Experiment 1 and tabulated as follows:

| 57-A | 57-B | 57-C | 57-D | 57-E | 57-F | 57-G | 57-H |
|---|---|---|---|---|---|---|---|
| 35.1 ± 3.8 | 0.9 ± 0.1 | 8.4 ± 2.1 | 0.3 ± 0.07 | 1.1 ± 0.3 | 0.6 ± 0.2 | 0.7 ± 0.15 | 0.4 ± 0.07 |

The results of Experiments 54 to 57 show the value provided by mixtures of stabilisers according to the invention with stabilisers belonging to the family of azoic compounds. There is in effect a synergistic effect using these two types of stabilisers as shown by the results of these Experiments.

EXPERIMENT 58

Doubled cards were used as described in Experiment 1 but of weight 870 g/m². These doubled cards were divided into six series 58-A to 58-F. Cards 58-A were each impregnated with 12.5g DDVP; the other doubled cards were each impregnated with 12.5g of a 1% solution in DDVP of one of the following compounds:
- 58-B : dibenzylsulphoxide
- 58-C : dibutylsulphoxide
- 58-D : 1,3-propanesultone
- 58-E : diethyl-4-nitrophenylphosphorothionate
- 58-F : 0,0-dimethyl-1,2,S-bis(ethoxycarbonyl)ethyl phosphorodithioate The thus impregnated cards were suspended in a room, the temperature of which was kept at 22° ± 2°C and of which the relative humidity of which was about 40.

At the end of 15 days, the percentage quantities of DDVP destroyed were measured as given in Experiment 1 and tabulated as follows:

| 58-A | 58-B | 58-C | 58-D | 58-E | 58-F |
|---|---|---|---|---|---|
| 31.6 ± 2.4 | 31.0 ± 2.0 | 28.8 ± 0.6 | 33.8 ± 1.0 | 29.6 ± 1.6 | 31.5 ± 2.2 |

EXPERIMENT 59

Doubled cards were used as described in Experiment 1 but of weight 895 g/m². These double cards were divided into four series 59-A to 59-D; cards 59-A were each impregnated with 12.5g DDVP; the other double cards were each impregnated with 12.5g of a 1.5% solution in DDVP of one of the following compounds:
- 59-B : tetramethylene sulfone
- 59-C : diphenyl sulfone
- 59-D : paratoluene sulfonic acid The thus impregnated cards were suspended in a room, the temperature of which was kept at 22° ± 2°C and of which the relative humidity was about 70.

At the end of 15 days, the percentage quantities of DDVP destroyed were measured as given in Experiment 1 and tabulated as follows:

| 59-A | 59-B | 59-C | 59-D |
|---|---|---|---|
| 36.8 ± 3.9 | 41.0 ± 1.0 | 36.1 ± 2.0 | 42.9 ± 2.1 |

The results of Experiments 58 and 59 show that it is not possible to stabilise a phosphoric ester such as DDVP with a sulphur compound different from those defined and recommended by the present invention.

Several formulations are described below with the object illustrating the invention but not of limiting it. For simplicity of expression the sulphur compounds used are denoted as follows:
- Compound A : 2-mercaptobenzothiazole
- Compound B : zinc salt of 2-mercaptobenzothiazole
- Compound C : bis(N,N-dimethylthiocarbamoyl) sulphide
- Compound D : bis(N,N-dimethylthiocarbamoyl) disulphide
- Compound E : thioacetamide
- Compound F : zinc N,N-dimethyldithiocarbamate
- Compound G : di-2-benzothiazolyl disulphide
- Compound H : methyl N,N-diethyldithiocarbamate
- Compound I : 1,3,5-trithiane The azoic compounds used in several cases as complementary stabilisers are denoted as follows, with the exception of azobenzene which is designated by its name:

| | |
|---|---|
| Diazo compound A: | 1-(4-phenylazophenylazo) 2-ethylaminonaphtalene |
| Diazo compound B: | 1-(3-methyl-2-nitrophenylazo) 3-ethoxycarbonyl-4,4-dimethyl-2,6-dioxo cyclohexane |

-continued

| | |
|---|---|
| Diazo compound C: | 1-phenylazo 2-naphthol |
| Diazo compound D: | 4-phenylazo N,N-diethylaniline |
| Diazo compound E: | chromium complex (1:2) in admixture of the following azoic compounds: 1-(2-hydroxy-5-nitrophenylazo) 2-naphthol sodium salt (0.4 mol) 1-(2-hydroxy-4-nitrophenylazo) 2-naphthol sodium salt (0.3 mol) 1-(2-hydroxy-3-nitro-5-tertamylphenylazo) 2-naphthol sodium salt (0.3 mol) |
| Diazo compound F: | chrome complex (1:2) in admixture of diazo compounds (2-amino-5-nitro-4-ethylsulphonyl phenol) 2(2-carboxyphenyl) naphtylamine, sodium salt and (2-amino-5-nitro-4-ethylsulphonylphenyl) →8-hydroxyquinoline, sodium salt. |

EXAMPLES 1 TO 10

Insecticidal compositions comprising DDVP as phosphoric ester and at least one divalent sulphur compound as principal stabiliser for this ester, these compositions also optionally containing a solvent for the ester and/or complementary stabiliser selected from azoic compounds and epoxidised compounds. Values in the following table and in the tables appended to the remainder of these examples are in parts by weight.

TABLE I

| DDVP | 1 98,8 | 2 98 | 3 99,3 | 4 75 | 5 70 | 6 78 | 7 65 | 8 85 | 9 90 | 10 50 |
|---|---|---|---|---|---|---|---|---|---|---|
| Dioctyl phthalate | — | — | — | 20 | 20 | — | — | — | — | 45 |
| Dibutyl sebacate | — | — | — | — | — | 20 | — | — | 9,2 | — |
| Diiso octyl-adipate | — | — | — | — | — | — | 33 | 10 | — | — |
| Azobenzene | — | — | 0,5 | — | — | — | — | — | 0,2 | — |
| Diazene D | — | — | — | — | — | 0,5 | — | — | — | — |
| Diazene E | — | — | — | — | 0,4 | — | — | — | 0,4 | — |
| Soya oil | — | — | — | 4,5 | — | — | — | — | — | — |
| octyl epoxy-stearate | — | — | — | — | 0,8 | — | — | — | — | — |
| Compound A | — | — | 0,2 | 0,5 | — | — | — | — | — | 5 |
| Compound D | 1,2 | — | — | — | — | — | — | — | 0,2 | — |
| Compound G | — | 2 | — | — | — | 1,5 | 2,0 | 5,0 | — | — |
| Compound H | — | — | — | — | 0,8 | — | — | — | — | — |

EXAMPLES 11 TO 20

Insecticidal compositions comprising DDVP as phosphoric ester at least one divanent sulphur compound as principal stabiliser therefor, a vaseline or paraffin oil as solvent, a heavy alkanone as co-solvent and in some cases a complementary stabiliser selected from azoic and epoxidised compounds.

TABLE II

| DDVP | 11 50 | 12 50 | 13 60 | 14 75 | 15 25 | 16 40 | 17 40 | 18 50 | 19 50 | 20 50 |
|---|---|---|---|---|---|---|---|---|---|---|
| Vaseline oil (i) | — | 35 | — | — | — | 48 | 48 | — | 36 | 36,5 |
| Paraffin oil (i') | 36,7 | — | 30 | 17 | 60 | — | — | 37 | — | — |
| Laurone | — | 13 | 9,9 | 6 | 12 | — | — | — | — | — |
| Palmitone | — | — | — | — | — | 10 | 10 | — | — | — |
| Stearone | 12,2 | — | — | — | — | — | — | 12,4 | 12,4 | 12,5 |
| cyclohexyl epoxystearate | — | — | — | — | — | 1 | — | — | — | — |
| epoxidised soya oil | — | — | — | — | — | — | 1,8 | — | — | — |
| Diazene B | 0,1 | — | — | — | — | — | — | — | 0,1 | 0,1 |
| Diazene C | — | — | 2 | 1 | — | — | — | 0,2 | — | — |
| Diazene D | — | — | — | — | 0,5 | — | — | — | — | — |
| Compound C | 1 | 2 | 0,1 | — | 2 | 1 | — | — | 1,5 | — |
| Compound E | — | — | — | 1 | — | — | — | 0,4 | — | — |
| Compound F | — | — | — | — | 0,5 | — | 0,2 | — | — | 0,8 |

(i) semi-refined oil having a density of 0.867 at 15°C and a gelation point of about 42°C
(i') semi-refined oil having a density of 0.870 at 15°C and a viscosity of 1°7 Engler at 50°C

EXAMPLES 21 TO 30

Insecticidal compositions comprising DDVP as phosphoric ester, at least one divalent sulphur compound as principal stabiliser therefor, a solid or semi-solid adjuvant selected from paraffin, vaseline and petrolatus, a solvent selected from heavy alkanones and in some cases a complementary stabiliser selected from azoic and epoxidised compounds.

TABLE III

| DDVP | 21 15 | 22 18 | 23 16 | 24 20 | 25 33 | 26 27 | 27 28 | 28 33 | 29 20 | 30 20 |
|---|---|---|---|---|---|---|---|---|---|---|
| ordinary paraffin 60/62° | — | 57 | 57 | 54 | — | — | — | — | 54 | 54 |
| ordinary paraffin 52/54° | 65 | — | — | — | — | — | — | — | — | — |
| vaseline (j) | — | — | — | — | 32 | 35 | — | 30 | — | — |

TABLE III-continued

| DDVP | 21<br>15 | 22<br>18 | 23<br>16 | 24<br>20 | 25<br>33 | 26<br>27 | 27<br>28 | 28<br>33 | 29<br>20 | 30<br>20 |
|---|---|---|---|---|---|---|---|---|---|---|
| petrolatum (j') | — | — | — | — | — | — | 35 | — | — | — |
| laurone | 19 | 23 | 23 | 24 | — | — | — | — | 24 | 24 |
| Stearone | — | — | — | — | 33 | 37 | 36 | 32 | — | — |
| epichlorohydrine | — | — | 3,5 | — | 1 | — | — | 2,5 | — | — |
| Diazene D | — | 0,2 | — | — | — | — | — | 0,5 | — | 0,5 |
| azobenzene | — | — | — | 0,4 | — | — | — | — | — | — |
| Compound B | 0,4 | — | — | 0,2 | — | — | 0,3 | 0,5 | 0,2 | — |
| Compound D | 0,6 | — | — | — | — | — | — | 1,5 | 0,8 | — |
| Compound C | — | 1,8 | — | 0,4 | 1 | — | 0,7 | — | — | — |
| Compound I | — | — | 0,5 | — | — | 1 | — | — | — | 0,5 |

(j) commercial product of yellow colour having a dropping point greater then 47°C
(j') chestnut coloured product having a dropping point of about 72°C.

EXAMPLES 31 TO 40

Insecticidal compositions usable in a wick evaporator formed by a reservoir and a wick dipping into the composition and having a part exposed to the free air. These compositions comprise DDVP as phosphoric ester, a solvent from the ester chosen from among alkanes, a co-solvent selected from chlorodecane, 3,6,9-trioxaundecane, and 5,8,11-trioxapentadecane, at least one divalent sulphur compound as principal stabiliser for the phosphoric ester and in some cases a complementary stabiliser selected from azoic and epoxidised compounds.

TABLE IV

| DDVP | 31<br>9,2 | 32<br>8,5 | 33<br>8,5 | 34<br>9,2 | 35<br>9,2 | 36<br>10,6 | 37<br>10,6 | 38<br>9,7 | 39<br>9,7 | 40<br>7,8 |
|---|---|---|---|---|---|---|---|---|---|---|
| n-dodecane | — | — | — | — | — | — | — | 85,1 | 85,2 | 85,9 |
| "Isoper L" (k") | 85,3 | 86 | 87,4 | 86,7 | 86,4 | 84,2 | 84,1 | — | — | — |
| 1-chloro decane | — | — | 4 | — | — | — | — | — | — | 6 |
| 3,6,9-trioxauedecane (k) | 5 | — | — | — | — | 5 | 5 | — | — | — |
| 5,8,11-trioxapentadecane (k') | — | 5 | — | 4 | 4 | — | — | 5 | 5 | — |
| epoxidised soya oil | 0,4 | — | — | — | — | — | — | — | — | 0,2 |
| Diazene A | 0,04 | 0,05 | — | — | — | — | 0,06 | — | — | — |
| azobenzene | — | — | — | — | 0,1 | — | 0,14 | — | — | — |
| Compound A | — | — | 0,1 | — | — | 0,05 | — | — | 0,1 | — |
| Compound H | 0,06 | 0,45 | — | 0,1 | 0,3 | 0,15 | 0,1 | 0,2 | — | 0,1 |

(k) co-solvent known under the name of diglycol diethyl ether and manufactured under the Trade Mark "diethylcarbitol" by the United States Company Union Carbide Chemicals Co. of New York.
(k') co-solvent known under the name of diglycol dibutyl ether sold under the Trade mark "dibutylcarbitol" by the Union Carbide Chemicals Co. aforementioned.
(k") distillation cut between 189 and 205°C of aliphatic branched chain hydrocarbons obtained by synthesis containing a mixture of decane, undecane and dodecane, produced by the company Esso Standard.

EXAMPLES 41 TO 50

Insecticidal compositions comprising DDVP as phosphoric ester, at least one divalent sulphur compound as principal stabiliser for this ester, an odorant material selected from linalol, ionone, methane, linalyl acetate, orange terpenes, and citron terpenes and in some cases a complementary stabiliser selected from azoic and epoxidised compounds.

TABLE V

| DDVP | 41<br>79,3 | 42<br>65 | 43<br>79,3 | 44<br>79,5 | 45<br>89 | 46<br>83 | 47<br>71 | 48<br>86 | 49<br>74,6 | 50<br>85 |
|---|---|---|---|---|---|---|---|---|---|---|
| Linalol | 7,5 | — | — | — | — | — | — | — | — | — |
| alpha ionone | — | — | — | 20 | 10 | — | — | — | 5 | — |
| Menthone | — | — | — | — | — | 15 | — | — | — | — |
| Flinalyl acetate | 7,5 | — | — | — | — | — | — | — | — | 12 |
| orange terpenes | — | 10 | 20 | — | — | — | — | — | 20 | — |
| citron terpenes | — | — | — | — | — | — | 25 | 12 | — | — |
| epoxidised soya oil | 5 | 2 | — | — | — | — | 2 | — | — | — |
| Diazene A | 0,5 | — | 0,2 | — | — | — | — | — | — | — |
| Diazene B | — | — | 0,4 | — | — | — | 0,5 | — | — | — |
| Compound A | 0,2 | 0,5 | — | — | — | — | — | — | — | — |
| Compound C | — | — | 0,1 | 0,5 | — | — | — | — | — | — |
| Compound D | — | 2,5 | — | — | — | — | — | 1 | — | — |
| Compound G | — | — | — | — | 1 | — | — | — | — | 3 |
| Compound H | — | — | — | — | — | 2 | — | 1 | — | — |
| Compound I | — | — | — | — | — | — | 1,5 | — | 0,4 | — |

EXAMPLES 51 TO 60

Insecticidal compositions comprising DDVP as phosphoric ester, at least one divalent sulphur compound as principal stabiliser, a synthetic thermoplastics resin as solid solvent, and a heavy ester used as co-solvent at the same time as in some cases as a plasticiser for the resin and in some cases a complementary stabiliser selected from azoic and epoxidised compounds:

EXAMPLE VI

| DDVP | 51<br>20 | 52<br>25 | 53<br>30 | 54<br>20 | 55<br>20 | 56<br>25 | 57<br>25 | 58<br>30 | 59<br>30 | 60<br>20,5 |
|---|---|---|---|---|---|---|---|---|---|---|
| polyvinyl chloride | 56 | 62 | 40 | 62 | 60 | 50 | — | — | — | 60 |
| ethylene/vinylacetate copolymer (n) | — | — | — | — | — | — | 54 | — | — | — |
| vinyl acetate vinyl chloride copolymer (10:90) | — | — | — | — | — | — | — | 50 | 54 | — |
| diiso octyl adipate | 23 | — | — | — | — | — | — | — | — | 9 |
| tricresyl phosphate | — | 10 | 29 | 12 | — | — | — | 19 | 5 | — |
| methyl laurate | — | — | — | 5 | 9 | — | — | — | — | — |
| dioctyl phthalate | — | — | — | — | 9 | 8 | 10 | — | — | — |
| dimethyl succinate | — | — | — | — | — | 15 | — | — | — | 9 |
| dimethyl maleate | — | — | — | — | — | — | 10 | — | 10 | — |
| octyl epoxystearate | — | 2 | — | — | 1 | — | — | — | — | — |
| epichlorohydrine | — | — | — | — | — | — | — | — | — | 0,5 |
| Diazene C | 0,6 | — | — | — | — | 0,2 | — | 0,8 | — | — |
| Diazene D | — | — | — | — | — | — | — | — | — | 0,5 |
| coloured pigment (m') | — | 0,5 | — | — | 0,5 | — | 0,4 | — | — | — |
| Compound B | — | 0,2 | — | — | — | — | — | — | — | 0,1 |
| Compound C | — | 0,3 | — | — | — | — | 0,6 | — | — | — |
| Compound D | 0,4 | — | 1 | 0,9 | — | — | — | — | 1 | 0,4 |
| Compound F | — | — | — | 0,1 | — | — | — | 0,2 | — | — |
| Compound G | — | — | — | — | 0,5 | 1,8 | — | — | — | — |

(m) copolymer of 67% ethylene of 33% vinyl acetate having an intrinsic viscosity of 0.78 for 0.25g in 100 ml toluene at 30°C.
(m') product sold under the Trade Mark "Blue Irgalith BL" and defined in the colour index under No. 74160 (pigment blue 15).

EXAMPLES 61 TO 70

Insecticidal compositions comprising DDVP as phosphoric ester, at least one divalent sulphur compound as principal stabiliser for this ester, a paraffin as solid adjuvant, a fossil silica as mineral adjuvant and in some cases a complementary stabiliser selected from azoic and epoxidised compounds, a copolymer of ethylene and vinyl acetate as an agent improving the mechanical properties of the paraffin, a pigment and/or a modified montmorillonite as dispersing agent permitting the homogeneity of the composition to be maintained before cooling.

TABLE VII

| DDVP | 61<br>23 | 62<br>25 | 63<br>25 | 64<br>25 | 65<br>24 | 66<br>24,5 | 67<br>24,5 | 68<br>24,5 | 69<br>24,25 | 70<br>24,25 |
|---|---|---|---|---|---|---|---|---|---|---|
| ordinary paraffin 60/62° | 60 | 57 | 46 | 46 | 54 | 54 | 58 | 58,5 | 65,5 | 65,5 |
| Copolymer of ethylene and vinyle acetate (71:29) | — | — | 12 | 12 | — | — | — | — | — | — |
| fossil diatoms | 15 | 16 | 15 | 15 | 15 | 15 | 15 | 15 | — | — |
| amin oleat (n') | — | — | — | — | 5 | 5 | — | — | — | — |
| modified monomorillonite (n") | — | — | — | — | — | — | 1 | 1 | 9,0 | 9,0 |
| pigment (n) | — | — | 1,0 | 0,8 | 0,5 | — | — | 0,6 | 0,5 | — |
| epoxidised soja oil | — | 0,5 | — | — | — | 0,7 | — | — | — | — |
| cyclohexyl epoxystearat | — | — | — | — | — | — | 0,9 | — | — | — |
| Azobenzene | — | 0,5 | — | — | 0,5 | — | — | — | — | — |
| Diazene B | — | — | — | 0,4 | — | — | 0,2 | — | — | — |
| Compound A | 1,5 | — | — | — | 0,3 | 0,8 | — | — | — | — |
| Compound B | 0,5 | 0,5 | — | — | 0,2 | — | — | — | 0,5 | — |
| Compound D | — | 0,5 | 0,9 | — | — | — | 0,4 | — | — | 0,9 |
| Compound F | — | — | — | 0,1 | — | — | — | — | — | 0,1 |
| Compound I | — | — | — | 0,8 | 0,5 | — | — | 0,4 | — | — |

(n) product sold under the mark "Yellow Irgalith BAW" and defined in the colour index under the No. 21100 (pigment yellow 13)
(n') product arising from the reaction in molecular ratio of 2:1 between oleic acid and a mixture of the following diamines: hexadecylaminopropylene (10%) octadecylaminopropylene amine (5%) octadecylaminopropylene amine (85%)
(n") a mixture of dimethyl dihexadecylammonium montmorillonite (70%) and dimethyl dioctadecylammonium montmorillonite.

TABLE VIII

| DDVP | 71<br>23,4 | 72<br>20,2 | 73<br>5,0 | 74<br>20,0 | 75<br>25,0 | 76<br>59,0 | 77<br>53,7 | 78<br>50 | 79<br>38,1 | 100<br>38,1 |
|---|---|---|---|---|---|---|---|---|---|---|
| ordinary paraffin 50/62° | 43,6 | 37,4 | 10,0 | — | 47,3 | — | — | — | — | — |
| Vaseline (j) | — | — | — | 2,0 | — | 31,5 | 28,8 | 26,9 | 38,3 | 38,4 |
| methyl laurate | — | — | — | — | — | — | — | — | — | 23,5 |
| stillene | — | — | — | — | — | 9,0 | — | — | — | — |
| phenoxy benzene | — | — | — | — | — | — | — | — | 23,0 | — |
| 1-chloro dodecane | 12,8 | — | — | 4,0 | — | — | 17,0 | — | — | — |
| tetrachloro biphenyl (p) | — | 22,6 | — | — | — | — | — | 23,1 | — | — |
| octachloro biphenyl (p') | — | — | 40,0 | 4,0 | 27,7 | — | — | — | — | — |

TABLE VIII-continued

| | 71 | 72 | 73 | 74 | 75 | 76 | 77 | 78 | 79 | 100 |
|---|---|---|---|---|---|---|---|---|---|---|
| DDVP | 23,4 | 20,2 | 5,0 | 20,0 | 25,0 | 59,0 | 53,7 | 50 | 38,1 | 38,1 |
| glass fibre | 5,0 | 5,0 | 43,0 | — | — | — | — | — | — | — |
| fossil diatoms | 14,0 | — | — | 25,0 | — | — | — | — | — | — |
| Kaolin | — | 14,5 | — | 43,0 | — | — | — | — | — | — |
| coloured pigment (m') | 1,0 | — | 1,8 | 2,0 | — | — | — | — | — | — |
| Compound D | 0,2 | — | — | — | — | 0,5 | 0,4 | — | 0,6 | — |
| Compound F | — | 0,3 | 0,2 | — | — | — | 0,1 | — | — | — |

(p) mixture of tetrachlorobiphenyls having a density between 1.447 and 1.457 at 25°C and sold under the Trade Mark "ELECTROPHENYL T" by the French Company Electrochemic Electrometallurgic acicrics d'Ugine.

(p') mixture of octachlorobiphenyls having a softening point of 110 ± 10°C sold under the Trade Mark "ELECTROPHENYL O" by the same company.

It is clear that the invention is not limited to the fomulations just set forth, which are merely given as examples of the manifold possibilities of use of the invention. In particular, the DDVP of these formulations can be replaced by a phosphoric ester chosen from:

1. 2,2-dichloro vinyl dimethyl phosphate
2. 2,2-dichloro vinyl diethyl phosphate
3. 2,2-dichloro vinyl dipropyl phosphate
4. 2,2-dichloro vinyl dibutyl phosphate
5. 2,2-dibromo vinyl dimethyl phosphate
6. 2,2-dibromo vinyl diethyl phosphate
7. 2,2-dibromo vinyl dipropyl phosphate
8. 2-bromo-2-chloro vinyl dimethyl phosphate
9. 2-bromo-2-chloro vinyl diethyl phosphate
10. 2,2-dichloro vinyl, ethyl methyl phosphate
11. 1,2-dibromo-2,2-dichloro ethyl dimethyl phosphate
12. 1,2-dibromo-2,2-dichloro ethyl diethyl phosphate
13. 1-bromo-2,2,2-trichloro ethyl dimethyl phosphate
14. 1-bromo-2,2,2-trichloro ethyl diethyl phosphate
15. 1,2,2,2-tetrabromo ethyl dimethyl phosphate
16. 1,2,2,2-tetrabromo ethyl diethyl phosphate
17. 1,2-dibromo-2,2-dichloro propyl dimethyl phosphate
18. 1,2-dibromo-2,2-dichloro propyl diethyl phosphate
19. 2,2-dichloro 1-methyl vinyl dimethyl phosphate
20. 2,2-dichloro 1-methyl vinyl diethyl phosphate
21. 2,2-dichloro vinyl dimethyl thiophosphate.

I claim:

1. An insecticidal composition on a fibrous porous support, said composition consisting essentially of
   I. about 5 to 99.5%, based on the weight of the composition, of an insecticidal phosphoric ester which partially decomposes by protonization displacement of a lower alkyl group of said phosphoric ester in favor of a hydrogen atom as a result of contacting said phosphoric acid ester with molecules of water, when exposing said ester to atmospheric humidity, thereby inhibiting said ester from being able to act against insects and which is a di($C_1$–$C_3$ alkyl) dihalogenovinyl phosphate; a di($C_1$–$C_3$ alkyl)dihalogenomethyl-1-vinyl phosphate; or a tetrahalogeno ($C_2$ or $C_3$ alkyl) di($C_1$ or $C_2$ alkyl) phosphate, wherein the halogen substituents are chlorine or bromine;
   II. about 0.05 to 10%, based on the weight of the phosphoric ester, of a sulphur-containing compound which effectively stabilizes the said pesticidal phosphoric acid ester against decomposition by protonization and having at least one divalent sulphur atom and said sulphur-containing compound having between 5 and 99% by weight of sulphur, based on the weight of the compound;
   and
   III. 0 to about 50%, based on the weight of the composition, of one or more inert mineral or organic adjuvants compatible with the phosphoric ester.

2. A composition according to claim 1 wherein the phosphoric ester is 2,2-dichlorovinyldimethyl phosphate.

3. An insecticidal composition consisting essentially of
   I. about 5 to 99.5%, based on the weight of the composition, of an insecticidal ester which partially decomposes by protonization displacement of a lower alkyl group of said phosphoric ester in favor of hydrogen atom as a result of contacting said phosphoric acid ester with molecules of water, when exposing said ester to atmospheric humidity, thereby inhibiting said ester from being able to act against insects and which is a di($C_1$–$C_3$ alkyl)-dihalogenovinyl phosphate; a di($C_1$–$C_3$ alkyl) dihalogenomethyl-1-vinyl phosphate; or a tetrahalogeno($C_2$ or $C_3$ alkyl)di($C_1$ or $C_2$ alkyl) phosphate, wherein the halogen substituents are chlorine or bromine;
   II. about 0.05 to 10%, based on the weight of the phosphoric ester, of a sulphur-containing compound which effectively stabilizes the said pesticidal phosphoric acid ester against decomposition by protonization and having at least one divalent sulphur atom and said sulphur-containing compound having between 5 and 99% by weight of sulphur, based on the weight of the compound
   III. 0.1 to 20% based on the weight of the pesticidal phosphoric ester, of an epoxidized compound or 0.1 to 10% based on the weight of the pesticidal phosphoric ester, of an azoic compound
   and
   IV. 0 to about 50%, based on the weight of the composition, of one or more inert mineral or organic adjuvants compatible with the phosphoric ester; the sulphur containing compound being selected from the group consisting of
   A. sulphanes of formula I

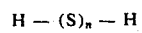   I.

when $n$ is a whole number from 1 to 6;
   B. mercaptans of formula II

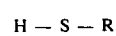   II.

in which R is a. a phenyl group,
b. a benzyl group,
c. a phenyl group or a benzyl group substituted by 1–3 alkyl groups containing 1–6 carbon atoms; 'd. an alkyl group containing 1–18 carbon atoms
e. a mono- or bicyclic heterocyclic group comprising 5 to 10 ring atoms in one or two fused rings, the first ring containing 1–3 ring members chosen from nitrogen, the group $$-\underset{|}{N}-R''$$

and oxygen, the remaining ring members consisting of the groups $$-\underset{\|}{C}-R''',$$

in which R'' is a group chosen from hydrogen, phenyl, and an alkyl or cycloalkyl group containing 1–10 carbon atoms and R''' is hydrogen, phenyl, or an alkyl group containing 1–4 carbon atoms and the second ring being a benzene ring,
f. a group (a) to (e) noted above carrying 1–3 substituents chosen from fluorine, chlorine and bromine,
g. a group (a) to (e) noted above substituted by a carboxy group, an alkoxycarbonyl group or a mercaptoalkoxycarbonyl group, containing 2 to 6 carbon atoms or an amino group of the formula $$-N{\Large<}_{R^V}^{R^{IV}}$$

wherein each of $R^{IV}$ and $R^V$, which may be the same or different, represents a hydrogen atom or an alkyl residue containing 1–10 carbon atoms or
h. a group of the formula $$-A-S-H$$

in which A represents an alkylene group containing 2–13 carbon atoms, or a phenylene, toluylene or 1,2-bis(methylene carbonyloxy)-ethylene group;

C. sulphides of formula III:

$$R_b - (S)_n - R'_b \qquad \text{III.}$$

in which n represents a whole number of 1 to 6 and each of $R_b$ and $R'_b$, which may be the same or different, is
a. an alkyl group of 1 to 18 carbon atoms,
b. phenyl,
c. benzyl,
d. morpholinyl
e. piperidyl,
f. pyridyl,
g. benzothiazolyl,
h. benzimidazolyl,
i. benzoxazolyl,
j. a group (a) to (i) mentioned above carrying 1–3 substituents selected from fluorine, chlorine, bromine, hydroxy, mercapto, nitro, cyano, carboxy, alkoxycarbonyl of up to 5 carbon atoms, and amino of the formula $$-N{\Large<}_{R^V}^{R^{IV}}$$

wherein $R^{IV}$ and $R^V$ are as hereinbefore defined and an alkyl containing 1–4 carbon atoms;

D. heterocyclic compounds which comprise 5 to 23 ring members forming 1 to 5 rings with at most 2 fused rings, which comprise 1–3 rings which each contain an —S— ring member and 2 other ring members chosen from the groups:

$$\underset{\|}{\overset{|}{C}}-R_1, \quad {\Large>}C{\Large<}_{R_3}^{R_2}, \quad =N-, \quad {\Large>}N-R_4$$

the remainder of the ring members being chosen from among the groupings:

$$\underset{\|}{\overset{|}{C}}-R_1 \text{ and } {\Large>}C{\Large<}_{R_3}^{R_2},$$

wherein $R_1$, $R_2$ and $R_3$ are independently hydrogen, chlorine, bromine, fluorine, alkyl of 1–5 carbon atoms, trifluoromethyl, nitro, or a group of the formula $$-N{\Large<}_{R^V}^{R^{IV}}$$

wherein $R^{IV}$ and $R^V$ are as hereinbefore defined or a group of the formula $$-S-N{\Large<}_{R^{VII}}^{R^{VI}}$$

in which each of $R^{VI}$ and $R^{VII}$, which may be the same or different, is hydrogen, phenyl, or alkyl of 1–18 carbon atoms, alkanoylamino containing 2–4 carbon atoms, mercapto, alkylthio containing 1–18 carbon atoms, oxo, thioxo, phenylazo, phenylazo carrying 1–2 substituents chosen from methyl, chloro, nitro and methoxy and $R_4$ is hydrogen or methyl; the heterocyclic compounds with fused rings being chosen from among those of which all the hetero ring members are in the same ring;

E. monocyclic saturated heterocyclic compounds having 6 ring members in which 1–3 ring members, which are not contiguous, are constituted by sulphur, one other ring member being a group of the formula $${\Large>}C{\Large<}_{R_3}^{R_2} \quad \text{or} \quad {\Large>}N-R_4,$$

and the remaining ring members being groups of the formula $${\Large>}C{\Large<}_{R_3}^{R_2}$$

in which $R_2$, $R_3$ and $R_4$ are as hereinbefore defined;

F. thioic compounds of formula IV:

$$R_c-Y-\underset{X}{\overset{\|}{C}}-Q \qquad \text{(IV)}$$

in which X and Y each represent an oxygen of sulphur atom, at least one of them being a sulphur atom;

a''. $R_c$ is hydrogen or alkyl of 1–6 carbon atoms, unsubstituted or substituted by a carboxy group, an alkoxycarbonyl group having 2 to 5 carbon atoms, a cycloalkyl or alkylcycloalkyl group containing 6 to 10 carbon atoms, a phenyl or benzyl group or an alkenyl group containing 2 to 5 carbon atoms;

and

Q is an alkyl group containing 1 to 6 carbon atoms, an alkyl group substituted by a cyano group, a cycloalkyl group containing 6 to 10 carbon atoms, a alkylcycloalkyl group containing 6 to 10 carbon atoms, a pyridyl or phenyl group or a phenyl group bearing one to three substituents chosen from fluorine, bromine, alkyl of 1 to 4 carbon atoms, nitro, and hydroxy, or Q is a group of the formula

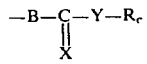

in which X, Y and $R_c$ are as hereinbefore defined and B is sulphur, a disulphide group, an alkylene group containing 1 to 8 carbon atoms or a 1,2-, 1,3- or 1,4-phenylene group or Q is a group of the formula

wherein Z is oxygen or sulphur atom and $R_c$ is as herein defined; or b''. $R_c$ and Q together from an alkylene group containing 3 to 10 carbon atoms in a branched or straight chain, or c''. Q represents a group of the formula

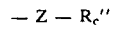

and $R_c$ and $R_c''$ together form a divalent group which is an aliphatic hydrocarbon chain containing 2 to 6 carbon atoms, a 1,2-, 1,3- or 1,4-phenylene group, a mono- or bicyclic system containing 5 to 10 ring members, one of the ring members being selected from the group consisting of hydrocarbons, the group =N- and the group

G. thiamides of formula V

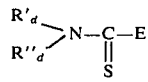

wherein either a. each of $R'_d$ and $R''_d$, which may be the same or different, represents hydrogen, alkyl of 1 to 4 carbon atoms or phenyl or $R'_d$ and $R''_d$ taken together from a straight or branched chain alkylene group containing 4 to 10 carbon atoms, and E represents an alkyl group containing 1 to 6 carbon atoms, an alkyl group substituted by a cyano group, a cycloalkyl group containing 6 to 10 carbon atoms, an alkylcycloalkyl group containing 6 to 10 carbon atoms, a pyridyl or phenyl group or a phenyl group bearing one to three substituents chosen from fluorine, bromine, alkyl of 1 to 4 carbon atoms, nitro and hydroxy or E represents a group of the formula

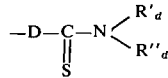

in which D represents a single bond or an alkylene group containing 1 to 8 carbon atoms or a phenylene group and $R'_d$ and $R''_d$ are as hereinbefore defined; or b. $R'_d$ and E together form an alkylene group containing 3 to 10 carbon atoms in a branched or straight chain; and $R''_d$ as the same meaning as hereinbefore defined;

H. dithiocarbamic esters of formula VI

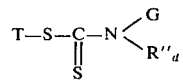 (VI)

in which $R''_d$ is hydrogen, alkyl of 1 to 4 carbon atoms or phenyl, and T represents an alkyl group containing 1 to 12 carbon atoms, an alkenyl group containing 2 to 12 carbon atoms, a benzyl group, a cycloalkyl or cyclozlkenyl group containing 5 to 6 carbon atoms, unsubstituted or substituted by 1 to 3 ($C_1$–$C_4$ alkyl) groups, or a phenyl group unsubstituted or substituted by 1 to 3 substituents chosen from alkyl and alkenyl groups containing up to 5 carbon atoms, chlorine and nitro; or T represents a group of the formula:

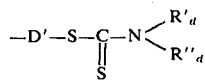

in which D' is a straight or branched alkylene group containing 2 to 6 carbon atoms and $R'_d$ and $R''_d$ are as hereinbefore defined, and G represents a group $R'''_d$ as defined above or a group of the formula

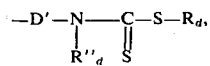

in which D' and $R''_d$ and $R'_d$ are as hereinbefore defined and $R_d$ represents an alkyl group containing 1 to 6 carbon atoms, an alkyl group substituted by a cyano group, a cycloalkyl group containing 6 to 10 carbon atoms, an alkylcycloalkyl group containing 6 to 10 carbon atoms, a pyridyl or phenyl group or a phenyl group bearing one to three substituents chosen from fluorine, bromine, alkyl of 1 to 4 carbon atoms, nitro and hydroxy;

I. thiocarbamic esters of formula VII

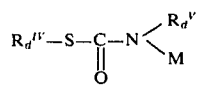 (VII)

in which $R^{IV}{}_d$ is alkyl of 1 to 18 carbon atoms, cycloalkyl or alkylcycloalkyl of 6 to 10 carbon atoms, phenyl unsubstituted or substituted by 1 to 3 substituents chosen from chlorine, nitro, and alkyl containing 1 to 4 carbon atoms, 2-benzimidazolyl, 2-benzoxazolyl or 2-benzothiazolyl and either:
   a. $R^V{}_d$ is a group $R'''{}_d$ as hereinbefore defined and M is hydrogen, alkyl of 1 to 4 carbon atoms or phenyl or a group of the formula

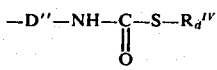

in which D'' is an unsubstituted or methyl-substituted 1,2-, 1,3- or 1,4-phenylene group and $R^{IV}{}_d$ is as hereinbefore defined; or
   b. $R^V{}_d$ and M together form an alkylene group containing 6 to 9 carbon atoms;

J. thiuram compounds of formula VIII

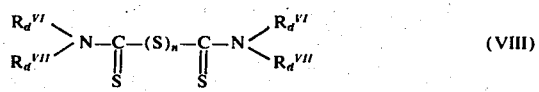

in which n is an integer of 1 to 6, $R^{VI}{}_d$ and $R^{VII}{}_d$ are groups $R_d'$ and $R_d''$ as hereinbefore defined or both $R^{VI}{}_d$ groups and/or both $R^{VII}{}_d$ groups together form a phenylene group or an alkylene group containing 2 to 3 carbon atoms, K. isothiocyanic esters of formula IX

in which $R_e$ is alkyl of 1 to 8 carbon atoms, phenyl unsubstituted or substituted by 1 to 3 groups chosen from alkyl of 1 to 5 carbon atoms, fluorine, chlorine, bromine, alkoxy and alkyl thio groups containing 1–4 carbon atoms and nitro;

L. thioureas of formula X

in which $R_f'''$ is hydrogen, allyl, phenyl, or alkyl of 1–4 carbon atoms and either
   a. W represents hydrogen, alkyl of 1–4 carbon atoms or allyl, and $R_f$ and $R_f''$ taken separately represent hydrogen, alkyl of 1 to 4 carbon atoms or allyl or $R_f$ and $R_f''$ taken together represent an ethylene group; or
   b. W represents a group of the formula

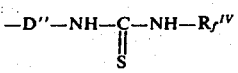

in which D'' is as hereinbefore defined and $R_f^{IV}$ is an alkoxy carbonyl residue containing 2 to 5 carbon atoms and $R_f$ and $R_f''$ each represent hydrogen;

M. thiiranes of formula XI

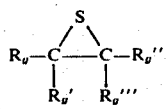
(XI)

in which either
   a. $R_g$ is hydrogen, alkyl of 1–6 carbon atoms, methyl substituted by one chlorine atom, phenyl, phenyl substituted by one chlorine atom, alkoxy of 1–4 carbon atoms, phenoxy or phenoxy carrying one or two substituents chosen from chlorine and methyl, and each of $R_g'$, $R_g''$ and $R_g'''$ which may be the same or different, is hydrogen or methyl; or
   b. $R_g$ is an 8-carboxyoctyl group or an 8-alkoxycarbonyloctyl group in which the alkoxy group contains 1–8 carbon atoms, $R_g'$ and $R_g'''$ are each hydrogen and $R_g''$ is an octyl or 2,3-epithiooctyl group;

N. sulphenamides of formula XII

in which $R_h$ is methyl, methyl bearing 1–3 substituents selected from chlorine and fluorine, ethyl, and ethyl bearing 1–5 substituents chosen from chlorine and fluorine, and
   I'. each of $R_h'$ and $R_h''$ represents hydrogen, alkyl of 1–4 carbon atoms, phenyl or cyclohexyl; or
   II'. $R_h'$ and $R_h''$ are chosen from the groups (I') and (II') as defined, the group (II') being chosen from methylsulphonyl, ethylsulphonyl, phenylsulphonyl, chlorophenyl, and $-SO_2-NX'X''$, in which X' and X'' are each methyl, ethyl, or phenyl; or
   III. $R_h'$ and $R_h''$, together with the nitrogen atom to which they are attached, form (a''') a cyclic system comprising 3–10 ring members and 1 or 2 rings, a second ring member, in addition to the said nitrogen atom, being a hydrocarbon member, sulphur, oxygen or nitrogen and the other ring members being hydrocarbon ring members, or (b''') a cyclic system as defined under (a''') substituted by one or two carbonyl oxygen atoms, O. sulphenic esters of formula XIII

in which $R_h$ is as hereinbefore defined and $R_h'''$ is selected from phenyl, phenyl carrying 1–3 substituents chosen from chlorine, nitro, and alkyl and alkoxy containing 1–4 carbon atoms, naphthyl and quinolyl;

P. thioketones of formula XIV

in which each of $R_i$ and $R_i'$, which may be the same of different, is alkyl of 1–4 carbon atoms, alkyl of 1–4 carbon atoms substituted by up to 9 fluorine atoms, cyclohexyl, phenyl, and phenyl carrying 1 or 2 substituents selected from alkyl and alkoxy groups containing 1–4 carbon atoms;

Q. salts derived from mercaptans defined under (B), (D) and (E) and in which the cation is a metal or an ammonium ion chosen from ions derived from ammonia, ions derived from an amine containing 1–3 alkyl groups of 1–4 carbon atoms, and derived from an aromatic amine, and anions derived from a nitrogen heterocycle;

R. salts derived from thioic acids defined under (F) and in which the cation is a metal or an ammonium ion chosen from ions derived from ammonia, ions derived from an amine containing 1–3 alkyl groups of 1–4 carbon atoms and derived from an aromatic amine, and ions derived from a nitrogen heterocycle; and S. salts derived from carbamic acids corresponding to thiocarbamic esters defined under (H) and (I) and in which the cation is a metal or an ammonium ion chosen from ions derived from ammonia, ions derived from an amine containing 1–3 alkyl groups of 1–4 carbon atoms and derived from an aromatic amine, and ions derived from a nitrogen heterocycle.

4. A composition according to claim 3 characterised in that the proportion of sulphur in the stabilising agent is at least 10% by weight.

5. A composition according to claim 3 wherein the proportion of stabilising agent is between 0.2 and 4% by weight of the phosphoric ester.

6. A composition according to claim 3 comprising the azoic compound in an amount of 0.1 to 10% based on the weight of the phosphoric pesticidal ester.

7. A composition according to claim 1, wherein the support is a porous or fibrous card.

* * * * *